(12) United States Patent
Yadav et al.

(10) Patent No.: US 12,721,731 B2
(45) **Date of Patent: *Sep. 1, 2026**

(54) EXPANDABLE INTERBODY DEVICE

(71) Applicant: MiRus LLC, Marietta, GA (US)

(72) Inventors: Jay Yadav, Atlanta, GA (US); Noah Roth, Marietta, GA (US); Charles Brenner, Marietta, GA (US); Wayne Gray, Mableton, GA (US); Jordan Bauman, Smyrna, GA (US); Ravi Enneti, Marietta, GA (US)

(73) Assignee: MiRus LLC, Marietta, GA (US)

( * ) Notice: Subject to any disclaimer, the term of this patent is extended or adjusted under 35 U.S.C. 154(b) by 2 days.

This patent is subject to a terminal disclaimer.

(21) Appl. No.: 18/977,012

(22) Filed: Dec. 11, 2024

(65) Prior Publication Data

US 2025/0114213 A1 Apr. 10, 2025

Related U.S. Application Data

(63) Continuation-in-part of application No. 29/978,028, filed on Dec. 11, 2024, and a continuation-in-part of application No. 29/978,019, filed on Dec. 11, 2024, and a continuation-in-part of application No. 18/653,439, filed on May 2, 2024, now Pat. No. 12,544,239.

(Continued)

(51) Int. Cl.
*A61F 2/44* (2006.01)

(52) U.S. Cl.
CPC .... *A61F 2/4425* (2013.01); *A61F 2220/0091* (2013.01)

(58) Field of Classification Search
CPC ...... A61F 2/442; A61F 2/4425; A61F 2/4455; A61F 2/447
USPC .......................................... 623/17.11–17.16
See application file for complete search history.

(56) References Cited

U.S. PATENT DOCUMENTS

2014/0107788 A1* 4/2014 Barreiro .................. A61F 2/442 623/17.16
2014/0194992 A1* 7/2014 Medina ................. A61F 2/4611 623/17.16

(Continued)

*Primary Examiner* — Eduardo C Robert
*Assistant Examiner* — Christina Negrellirodriguez
(74) *Attorney, Agent, or Firm* — UB Greensfelder LLP; Brian E. Turung

(57) ABSTRACT

An expandable interbody device used as a prosthesis during spinal surgery. The expandable interbody device is configured to be inserted into the space between spinal discs to provide stability. The expandable interbody device includes a drive block, a top endplate, a bottom endplate, a first drive arrangement, and a second drive arrangement; the first drive arrangement includes a first drive screw, a first left side slide, a second left side slide, a first upper left side linkage, a second upper left side linkage, a first lower left side linkage age and a second lower left side linkage; and the second drive arrangement includes a second drive screw, a first right side slide, a second right side slide, a first upper right side linkage, a second upper right side linkage, a first lower right side linkage and a second lower right side linkage. The drive block is configured to move relative to the top and bottom endplates as the top and bottom endplates move between a fully closed and a fully expanded position.

27 Claims, 17 Drawing Sheets

Related U.S. Application Data

(60) Provisional application No. 63/534,649, filed on Aug. 25, 2023.

(56) References Cited

U.S. PATENT DOCUMENTS

| | | | | |
|---|---|---|---|---|
| 2014/0277473 | A1* | 9/2014 | Perrow | A61F 2/4455 623/17.15 |
| 2022/0183854 | A1* | 6/2022 | Altarac | A61F 2/4611 |
| 2025/0064598 | A1* | 2/2025 | Bauman | A61F 2/447 |

* cited by examiner

EXPANDABLE INTERBODY DEVICE

REFERENCED APPLICATIONS

The present patent application is a continuation-in-part of U.S. Ser. No. 18/653,439 filed May 2, 2024, which in turn claims the benefit of U.S. Provisional Patent Application Ser. No. 63/534,649 filed Aug. 25, 2023 and entitled "Expandable Interbody Device", the disclosure of which is hereby incorporated by reference herein in its entirety and made part of the present U.S. utility patent application for all purposes.

The present patent application is a continuation-in-part of U.S. Ser. No. 29/978,019 filed Dec. 11, 2024, the disclosures of which is hereby incorporated by reference herein in its entirety and made part of the present U.S. utility patent application for all purposes.

The present patent application is a continuation-in-part of U.S. Ser. No. 29/978,028 filed Dec. 11, 2024, the disclosures of which is hereby incorporated by reference herein in its entirety and made part of the present U.S. utility patent application for all purposes.

TECHNICAL FIELD

The present disclosure relates generally to medical device, more particularly to an expandable interbody device that can be used as a prosthesis during spinal surgery. The expandable interbody device is configured to be inserted into the space between spinal disks to provide stability. The expandable interbody device can be introduced between vertebrae of a patient's spine for fixation with bone to immobilize the joint as part of a surgical treatment.

BACKGROUND OF DISCLOSURE

Intervertebral fusion devices for the cervical and lumbar spine have been used for many years. These devices are originally inserted into a disc space after the coring out of a bone graft from the hip. This technique is currently not commonly practiced due to disadvantages such as lengthy operation times, destruction of a large portion of the disc space, high risk of nerve injury, and hip pain after harvesting the bone graft.

A current device commonly used to perform the intervertebral portion of an intervertebral body fusion is an intervertebral body fusion device and a distraction device.

The intervertebral body fusion device can be implanted as a standalone device or implanted in combination with other devices such as pedicle screws and rods. The intervertebral body fusion device distracts a collapsed disc, decompresses the nerve root, and allows load sharing to enhance bone formation. The intervertebral body fusion device is configured to be small enough to allow implantation with minimal retraction and pulling on nerves.

In a typical intervertebral body fusion procedure, a portion of the intervertebral disc is first removed from between the vertebral bodies. The distraction device is then inserted into the cleared space to enlarge the disc space and the vertebral bodies are separated by the distraction device. Thereafter, the intervertebral fusion device is inserted into the distracted space. U.S. Pat. Nos. 8,409,291; 9,439,771; 9,486,328; 10,881,531; 11,278,423; 11,285,014; and US Publication No. 2022/0168116 disclose prior art intervertebral body fusion devices; all of which are incorporated herein by reference.

In view of the current state of the art of intervertebral body fusion device, there is a continued need for an improved intervertebral body fusion device.

SUMMARY OF DISCLOSURE

The present disclosure is directed to an expandable interbody device that can be used as a prosthesis during spinal surgery. The expandable interbody device is configured to be inserted into the space between spinal disks to provide stability. The expandable interbody device can be introduced between vertebrae of a patient's spine (e.g., in the disk space between adjacent vertebrae) for fixation with bone to immobilize the joint as part of a surgical treatment.

In one non-limiting aspect of the present disclosure, the expandable interbody device is configured to vertically expand on the first and/or second sides along a longitudinal length of the expandable interbody device. In one non-limiting embodiment, the expandable interbody device can a) be independently vertically expanded along a first side while the second side is not vertically expanded; b) be independently vertically expanded along a second side while the first side is not vertically expanded; c) be vertically expanded the same amount along both the first and second sides; and/or d) be vertically expanded along the first side which is different from the vertical expansion along the second side. When the first and second sides are vertically expanded, the vertical expansion can a) be the same amount for both the first and second sides, b) be a different amount for the first and second sides, c) occur at the same time for the first and second sides, and/or d) occur at different times for the first and second sides.

In another and/or alternative aspect of the present disclosure, the expandable interbody device is configured to vertically expand both on the first and second sides along a longitudinal length of the expandable interbody device, and the expandable interbody device includes first and second drive arrangements wherein the first drive arrangement is configured to cause the first side of the expandable interbody device to expand vertically, and wherein the second drive arrangement is configured to cause the second side of the expandable interbody device to expand vertically. In one non-limiting embodiment, the first and second drive arrangements can be operated independently from one another.

In another and/or alternative aspect of the present disclosure, the expandable interbody device includes one or more drive arrangements. Each drive arrangement includes at least one linkage, and a slide block. In one non-limiting configuration, each drive arrangement includes first and second linkages, first and second slide blocks, and a drive screw. In another non-limiting arrangement, the drive screw is configured to cause one or more of the slide blocks to move along a longitudinal axis of the expandable interbody device when the drive screw is rotated. In another non-limiting configuration, the drive screw is configured to cause the first and second slide blocks to move along a longitudinal axis of the expandable interbody device when the drive screw is rotated, and wherein the first slide block moves along a longitudinal axis of the expandable interbody device in an opposite direction from movement of the second slide block along a longitudinal axis of the expandable interbody device when the drive screw is rotated.

In another and/or alternative aspect of the present disclosure, the expandable interbody device includes a main housing or drive block or core, top and bottom endplates, and one or more drive arrangements. Each drive arrangement includes at least one linkage, and a slide block. One or more drive screws are used to cause the slide block to move relative to the main housing when the drive screw is rotated. Each of the drive screws is rotatable connected to the main housing or drive block or core. In one non-limiting embodiment, one or more of the drive screws is rotatable connected to the main housing or drive block or core and remains in position along a longitudinal axis of the expandable interbody and/or main housing or drive block or core when the drive screw is rotated. In one non-limiting arrangement, the drive screw moves 0-5% (and all values and ranges therebetween) along the longitudinal length of the main housing or the expandable interbody device during the rotation of the drive screw. In another non-limiting embodiment, each linkage has first and second end portions, wherein the first end portion is rotatably or pivotally connected to a slide block and the second end portion is engaged with and/or is rotatably or pivotally connected to either the top or bottom endplates. In another non-limiting embodiment, at least a portion of the top endplate is configured to move upwardly from the main housing or drive block or core when one or more drive screws are rotated. In another non-limiting embodiment, at least a portion of the bottom endplate is configured to move downwardly from the main housing or drive block or core when one or more of the drive screws are rotated. In another non-limiting embodiment, the one or more slide blocks are configured to move along the longitudinal length of the expandable interbody device or main housing or drive block or core. In one non-limiting arrangement, the one or more slide blocks are configured to do not move upwardly or downwardly from the main housing or drive block or core when one or more of the drive screws are rotated.

In another and/or alternative aspect of the present disclosure, the expandable interbody device includes a main housing or drive block or core, top and bottom endplates, and a first drive arrangement. The first drive arrangement causes the first side edge of each of the top and bottom endplates to move a same distance from the main housing or drive block or core when the drive screw for the first drive arrangement is rotated. In another non-limiting embodiment, the expandable interbody device includes a main housing or drive block or core, top and bottom endplates, and a second drive arrangement. The second drive arrangement causes the second side edge of each of the top and bottom endplates to move a same distance from the main housing or drive block or core when the drive screw for the second drive arrangement is rotated. In one non-limiting embodiment, the first and second drive arrangements can be independently operated from one another.

In another and/or alternative aspect of the present disclosure, the expandable interbody device includes a main housing or drive block or core, top and bottom endplates, and one or more drive arrangements, and wherein each drive arrangement includes at least one linkage, and a slide block. A drive screw is provided wherein the drive screw threadedly engages the slide block. In one non-limiting embodiment, there is provided a first drive arrangement that includes first and second slide blocks, and first and second sets of linkages on each of the slide blocks, wherein each set of linkages includes first and second linkages. In another non-limiting embodiment, there is provided a second drive arrangement that includes first and second slide blocks, and first and second sets of linkages on each of the slide blocks, wherein each set of linkages includes first and second linkages. In another non-limiting embodiment, there is provided a first drive screw that threadedly engages the first and second slide blocks of the first drive arrangement. In one non-limiting arrangement, the first drive screw is simultaneously threadedly engaged with the first and second slide blocks of the first drive arrangement and causes the first and second slide blocks to simultaneously move (e.g., simultaneously move toward one another, simultaneously move away from one another) when the first drive screw is rotated. In another non-limiting arrangement, the first drive screw moves 0-5% (and all values and ranges therebetween) along the longitudinal length of the main housing or the expandable interbody device during the rotation of the first drive screw. In another non-limiting embodiment, there is provided a second drive screw that threadedly engages the first and second slide blocks of the second drive arrangement. In one non-limiting arrangement, the second drive screw is simultaneously threadedly engaged with the first and second slide blocks of the second drive arrangement and causes the first and second slide blocks to simultaneously move (e.g., simultaneously move toward one another, simultaneously move away from one another) when the second drive screw is rotated. In another non-limiting arrangement, the second drive screw moves 0-5% (and all values and ranges therebetween) along the longitudinal length of the main housing or the expandable interbody device during the rotation of the second drive screw.

In another and/or alternative aspect of the present disclosure, the expandable interbody device optionally includes one or more graft windows. One or more graft windows, when used, can be to facilitate in fusion of the expandable interbody device with surrounding tissue and/or bone due to tissue and/or bone growing into and/or about the one or more graft windows.

In another and/or alternative aspect of the present disclosure, the expandable interbody device optionally includes top and bottom endplates, wherein the top surface of one or both of the top and bottom endplates include a micro-textured surface and/or one or more teeth.

In another and/or alternative aspect of the present disclosure, the expandable interbody device includes top and bottom endplates that have a generally planar top surface (e.g., the top surface of the endplate without consideration of any surface structures or gripping structures on the top surface) and wherein at least 50% (e.g., 50-100% and all values and ranges therebetween) optionally lie in generally parallel planes (e.g., ±5° and all values and ranges therebetween) when the top and bottom endplates are in the fully contracted and the fully expanded positions.

In another and/or alternative aspect of the present disclosure, the expandable interbody device includes top and bottom endplates each having front and rear ends that are optionally spaced from one another as the expandable interbody device moves between the fully contracted and fully expanded positions.

In another and/or alternative aspect of the present disclosure, the expandable interbody device optionally include one or more side guide arrangements to a) facilitate in maintaining the longitudinal position of the drive block or core relative to the top and bottom endplates as the endplates move between the fully closed and fully expanded positions, b) facilitate in maintaining the longitudinal position of the top and bottom endplates relative to drive block or core as the endplates move between the fully closed and fully expanded positions, or c) facilitate in the longitudinal movement of the drive block or core relative to the top and bottom endplates as the endplates move between the fully closed and fully expanded positions. In one non-limiting embodiment, the one or more side guide arrangements facilitate in preventing the longitudinal movement of the drive block or core relative to the top and bottom endplates as the top and bottom endplates move between the fully closed and fully expanded positions. In one non-limiting configuration, the expandable interbody device includes a side guide arrangement on or both sides of the expandable interbody device, and wherein the bottom endplate includes a bottom side guide or slot or flange and/or the top endplate includes a top side guide or slot or flange, and wherein the drive block or core includes one or more block guides or guide slots or flanges that are configured to engage the top and/or bottom side guides or slots or flange and facilitate preventing the longitudinal movement of the drive block or core relative to the top and bottom endplates as the top and bottom endplates move between the fully closed and fully expanded positions. In another non-limiting embodiment, the one or more side guide arrangements facilitate in controlling the longitudinal movement of the drive block or core relative to the top and bottom endplates as the top and bottom endplates move between the fully closed and fully expanded positions, or vice versa. In one non-limiting configuration, the expandable interbody device includes a side guide arrangement on or both sides of the expandable interbody device, and wherein the bottom endplate includes a bottom side guide or slot or flange and/or the top endplate includes a top side guide or slot or flange, and wherein the drive block or core includes one or more block guides or guide slots or flanges that are configured to engage the top and/or bottom side guides and facilitate controlling that amount of longitudinal movement of the drive block or core relative to the top and bottom endplates as the top and bottom endplates move between the fully closed and fully expanded positions, and/or facilitate controlling that amount of longitudinal movement of the top and bottom endplates relative to the drive block or core as the top and bottom endplates move between the fully closed and fully expanded positions. In another non-limiting configuration, the position of the front end of the drive block or core is caused to be located more forwardly relative to the front ends of the top and bottom endplates as the top and bottom endplates move from the fully closed and fully expanded positions. In another non-limiting configuration, the position of the front end of the drive block or core is caused to be located more rearwardly relative to the front ends of the top and bottom endplates as the top and bottom endplates move from the fully closed and fully expanded positions. In another non-limiting embodiment, the one or more side guide arrangements facilitate in limiting or preventing the longitudinal movement of the drive block or core relative to the top and bottom endplates as the top and bottom endplates move between the fully closed and fully expanded positions, or vice versa. In one non-limiting configuration, the expandable interbody device includes a side guide arrangement on or both sides of the expandable interbody device, and wherein the bottom endplate includes a bottom side guide or slot or flange and/or the top endplate includes a top side guide or slot or flange, and wherein the drive block or core includes one or more block guides or guide slots or flanges that are configured to engage the top and/or bottom side guides or slots or flanges and facilitate limiting or preventing longitudinal movement of the drive block or core relative to the top and bottom endplates as the top and bottom endplates move between the fully closed and fully expanded positions, and/or facilitate controlling that amount of longitudinal movement of the top and bottom endplates relative to the drive block or core as the top and bottom endplates move between the fully closed and fully expanded positions.

In another and/or alternative aspect of the present disclosure, the expandable interbody device is optionally partially or fully formed of refractory metal alloy or metal alloy that includes at least 15 atw. % rhenium. As defined herein, a refractory metal alloy is a metal alloy that includes at least 20 wt. % of one or more of molybdenum, rhenium, niobium, tantalum, or tungsten. Non-limiting metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc.

In another and/or alternative non-limiting aspect of the disclosure, one or more or all of the components of the expandable interbody device is partially or fully formed of a metal alloy. In one non-limiting embodiment, a portion or all of the one or more or all of the components of the expandable interbody device is formed of a metal alloy selected from a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 atomic weight percent (awt. %) or atomic percent (awt. %) rhenium (e.g., 5-99 awt. % rhenium and all values and ranges therebetween). As used herein, atomic weight percent (awt. %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents. As defined herein, a stainless-steel alloy (SS alloy) includes 10-28 wt. % (weight percent) chromium, 0-35 wt. % nickel, 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, 0-2 wt. % tungsten, and at least 50 wt. % iron. One non-limiting stainless-steel alloy is 316L stainless-steel that includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 15-32 wt. % chromium, 1-38 wt. % nickel, 2-18 wt. % molybdenum, 0-18 wt. % iron, 0-1 wt. % titanium, 0-0.15 wt. % manganese, 0-0.15 wt. % silver, 0-0.25 wt. % carbon, 0-16 wt. % tungsten, 0-2 wt. % silicon, 0-2 wt. % aluminum, 0-1 wt. % iron, 30-68 wt. % cobalt, 0-0.1 wt. % boron, 0-0.15 wt. % silver, and 0-2 wt. % titanium. One type of cobalt-chromium alloy is MP35N alloy that includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. Two other types of cobalt-chromium alloy are Phynox and Elgiloy alloy that include 38-42 wt. % cobalt, 18-22 wt. % chromium, 14-18 wt. % iron, 13-17 wt. % nickel, 6-8 wt. % molybdenum. Another type of cobalt-chromium alloy is L605 alloy that includes 18-22 wt. % chromium, 14-16 wt. % tungsten, 9-11 wt. % nickel, balance cobalt. As defined herein, a titanium-aluminum-vanadium alloy (TiAlV alloy) includes 5.5-6.75 wt. % aluminum, 3.5-4.5 wt. % vanadium, 85-93 wt. % titanium, 0-0.4 wt. % iron, 0-0.2 wt. % carbon.

One type of titanium-aluminum-vanadium alloy is Ti-6Al-4V alloy that includes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, 0-8 wt. % nickel, 0-5 wt. % copper, 0-5 wt. % molybdenum, 0-4 wt. % iron. As defined herein, a molybdenum alloy includes 90-99.5 wt. % molybdenum, 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, 0-1 wt. % cobalt, and 0-0.5 wt. % silicon. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc. In one non-limiting embodiment, one or more or all of the components of the expandable interbody device is partially or fully formed of a metal alloy that includes at least 15 awt. % rhenium so as to improve the ductility and/or tensile strength of the metal alloy as compared to a metal alloy is that absent rhenium. Such improvement in ductility and/or tensile strength due to the inclusion of at least 15 awt. % rhenium in the metal alloy is referred to as the "rhenium effect." As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. In another non-limiting embodiment, the first and/or second endplates of the expandable interbody device are partially or fully formed of titanium alloy, molybdenum alloy rhenium alloy, or metal alloy that includes at least 5 awt. % rhenium. In another non-limiting embodiment, the drive block, pins, linkage block, drive screw, and/or linkages are partially or fully formed of titanium alloy, molybdenum alloy rhenium alloy, or metal alloy that includes at least 5 awt. % rhenium. The material used to form the different components of the expandable interbody device can be the same or different.

In another and/or alternative non-limiting aspect of the disclosure, one or more portions of the outer surface of the expandable interbody device can be coated with an enhancement layer. Non-limiting enhancement layers include chromium nitride (CrN), diamond-like carbon (DLC), titanium nitride (TiN), titanium oxynitride or titanium nitride oxide (TiNOx), zirconium nitride (ZrN), zirconium oxide (ZrO2), zirconium oxynitride (ZrNxOy) [e.g., cubic ZrN:O, cubic ZrO2:N, tetragonal ZrO2:N, and monoclinic ZrO2:N phase coatings], oxyzirconium-nitrogen-carbon (ZrNC), zirconium OxyCarbide (ZrOC), and combinations of such coatings. In one non-limiting embodiment, the one or more enhancement layers are optionally applied to a portion or all of the outer surface of the expandable interbody device by use of a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. In another non-limiting embodiment, the thickness of the enhancement layer is greater than 1 nanometer (e.g., 2 nanometers to 100 microns and all values and ranges therebetween), and typically 0.1-25 microns, and more typically 0.2-10 microns. In another non-limiting embodiment, the hardness of the enhancement layer can be at least 5 GPa (ASTM C1327-15 or ASTM C1624-05), typically 5-50 GPa (and all values and ranges therebetween), more typically 10-25 GPa, and still more typically 14-24 GPa. In another non-limiting embodiment, the coefficient of friction (COF) of the enhancement layer can be 0.04-0.2 (and all values and ranges therebetween), and typically 0.6-0.15. In another non-limiting embodiment, the wear rate of the enhancement layer can be 0.5×10-7 mm3/N-m to 3×10-7 mm3/N-m (an all values and ranges therebetween), and typically 1.2×10-7 mm3/N-m to 2×10-7 mm3/N-m. In another non-limiting embodiment, the enhancement layer includes no more than 0.1 wt. % nickel, no more than 0.1 wt. % chromium, and/or no more than 0.1 wt. % cobalt. In another non-limiting embodiment, the outer surface of the metal portion of the expandable interbody device includes no more than 0.1 wt. % nickel, no more than 0.1 wt. % chromium, and/or no more than 0.1 wt. % cobalt. The adhesion layer, when used to facilitate in adhering the enhancement layer to the expandable interbody device, includes no more than 0.1 wt. % nickel, no more than 0.1 wt. % chromium, and/or no more than 0.1 wt. % cobalt. In accordance with another non-limiting embodiment, the chromium nitride (CrN) coating generally includes 40-85 wt. % Cr (and all values and ranges therebetween), 15-60 wt. % N (and all values and ranges therebetween), 0-10 wt. % Re (and all values and ranges therebetween), 0-10 wt. % Si (and all values and ranges therebetween), 0-2 wt. % O (and all values and ranges therebetween), and 0-2 wt. % C (and all values and ranges therebetween). In another non-limiting embodiment, the diamond-Like Carbon (DLC) coating generally includes 60-99.99 wt. % C (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % O (and all values and ranges therebetween). In another non-limiting embodiment, the ratio of N to O when forming the TiNOx coating is generally 1:10 to 10:1 (and all values and ranges therebetween). In another non-limiting embodiment, the enhancement layer composition generally includes 20-85 wt. % Ti (and all values and ranges therebetween), 0.5-35 wt. % N (and all values and ranges therebetween), 0-10 wt. % Re (and all values and ranges therebetween), and 0.5-35 wt. % O (and all values and ranges therebetween). In another non-limiting embodiment, the enhancement layer composition generally includes 35-90 wt. % Zr (and all values and ranges therebetween), 5-25 wt. % N (and all values and ranges therebetween), 0-10 wt. % Re (and all values and ranges therebetween), 0-20 wt. % Si (and all values and ranges therebetween), 0-2 wt. % O (and all values and ranges therebetween), and 0-2 wt. % C (and all values and ranges therebetween). In another non-limiting embodiment, the enhancement layer composition generally includes 35-90 wt. % Zr (and all values and ranges therebetween), 10-35 wt. % O (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % C (and all values and ranges therebetween). In another non-limiting embodiment, the enhancement layer composition generally includes 40-95 wt. % Zr (and all values and ranges therebetween), 5-25 wt. % O (and all values and ranges therebetween), and 10-40 wt. % C (and all values and ranges therebetween), 0-2 wt. % N (and all values and ranges therebetween), 0-10 wt. % Re (and all values and ranges therebetween), and 0-20 wt. % Si (and all values and ranges therebetween). In another non-limiting embodiment, the enhancement layer composition generally includes 20-85 wt. % Zr (and all values and ranges therebetween), 0.5-35 wt. % N (and all values and ranges therebetween), and 0.5-35 wt. % O (and all values and ranges therebetween). In another non-limiting embodiment, the enhancement layer composition generally includes 40-95 wt. % Zr (and all values and ranges therebetween), 5-40 wt. % N (and all values and ranges therebetween), and 5-40 wt. % C (and all values and ranges therebetween), 0-2 wt. % O (and all values and ranges therebetween), 0-10 wt. % Re (and all values and ranges therebetween), and 0-20 wt. % Si (and all values and ranges therebetween).

In yet another and/or alternative non-limiting aspect of the present disclosure, the expandable interbody device can include, contain, and/or be coated with one or more agents that facilitate in the success of the expandable interbody device and/or treated area. The term “agent” includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungal, and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. The type and/or amount of agent included in and/or coated on the expandable interbody device can vary. When two or more agents are included in and/or coated on the expandable interbody device, the amount of two or more agents can be the same or different. The type and/or amount of agent included on, in, and/or in conjunction with expandable interbody device are generally selected to address one or more clinical events. Typically, the amount of agent included on, in, and/or used in conjunction with the expandable interbody device is about 0.01-100 μg per $mm^2$ and/or at least about 0.00001 wt. % of device; however, other amounts can be used. In one non-limiting embodiment of the disclosure, the expandable interbody device can be partially or fully coated and/or impregnated with one or more agents to facilitate in the success of a particular medical procedure. The amount of the two of more agents on, in, and/or used in conjunction with the expandable interbody device can be the same or different. The one or more agents can be coated on and/or impregnated in the expandable interbody device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition.

In a further and/or alternative non-limiting aspect of the present disclosure, the one or more agents on and/or in the expandable interbody device (when used) can be released in a controlled manner so the area to be treated is provided with the desired dosage of agent over a sustained period of time. As can be appreciated, controlled release of one or more agents on the expandable interbody device is not always required and/or desirable. As such, one or more of the agents on and/or in the expandable interbody device can be uncontrollably released from the expandable interbody device during and/or after insertion of the expandable interbody device in the treatment area. It can also be appreciated that one or more agents on and/or in the expandable interbody device can be controllably released from the expandable interbody device and one or more agents on and/or in the expandable interbody device can be uncontrollably released from the expandable interbody device. It can also be appreciated that one or more agents on and/or in one region of the expandable interbody device can be controllably released from the expandable interbody device and one or more agents on and/or in the expandable interbody device can be uncontrollably released from another region on the expandable interbody device. As such, the expandable interbody device can be designed such that 1) all the agent on and/or in the expandable interbody device is controllably released, 2) some of the agent on and/or in the expandable interbody device is controllably released and some of the agent on the expandable interbody device is non-controllably released, or 3) none of the agent on and/or in the expandable interbody device is controllably released. The expandable interbody device can also be designed such that the rate of release of the one or more agents from the expandable interbody device is the same or different. The expandable interbody device can also be designed such that the rate of release of the one or more agents from one or more regions on the expandable interbody device is the same or different. Non-limiting arrangements that can be used to control the release of one or more agents from the expandable interbody device include 1) at least partially coating one or more agents with one or more polymers, 2) at least partially incorporating and/or at least partially encapsulating one or more agents into and/or with one or more polymers, and/or 3) inserting one or more agents in pores, passageway, cavities, etc., in the expandable interbody device and at least partially coating or covering such pores, passageway, cavities, etc., with one or more polymers. As can be appreciated, other or additional arrangements can be used to control the release of one or more agents from the expandable interbody device.

In another and/or alternative non-limiting aspect of the present disclosure, the expandable interbody device, when including and/or coated with one or more agents, can include and/or be coated with one or more agents that are the same or different in different regions of the expandable interbody device and/or have differing amounts and/or concentrations in differing regions of the expandable interbody device. For instance, the expandable interbody device can be 1) coated with and/or include one or more biologicals on at least one portion of the expandable interbody device and at least another portion of the expandable interbody device is not coated with and/or includes agent; 2) coated with and/or include one or more biologicals on at least one portion of the expandable interbody device that is different from one or more biologicals on at least another portion of the expandable interbody device; and/or 3) coated with and/or include one or more biologicals at a concentration on at least one portion of the expandable interbody device that is different from the concentration of one or more biologicals on at least another portion of the expandable interbody device; etc.

In still yet another and/or alternative non-limiting aspect of the present disclosure, one or more portions of the expandable interbody device can 1) include the same or different agents, 2) include the same or different amount of one or more agents, 3) include the same or different polymer coatings, 4) include the same or different coating thicknesses of one or more polymer coatings, 5) have one or more portions of the expandable interbody device controllably release and/or uncontrollably release one or more agents, and/or 6) have one or more portions of the expandable interbody device controllably release one or more agents and one or more portions of the expandable interbody device uncontrollably release one or more agents.

In yet another and/or alternative non-limiting aspect of the disclosure, the expandable interbody device can include a marker material that facilitates enabling the expandable interbody device to be properly positioned in a treatment area. The marker material is typically designed to be visible to electromagnetic waves (e.g., x-rays, microwaves, visible light, infrared waves, ultraviolet waves, etc.) and/or sound waves (e.g., ultrasound waves, etc.); magnetic waves (e.g., MRI, etc.). In one non-limiting embodiment, the marker material is visible to x-rays (i.e., radiopaque). The marker material can form all or a portion of the expandable interbody device and/or be coated on one or more portions (flaring portion and/or body portion, at ends of expandable interbody device, at or near transition of body portion and flaring section, etc.) of the expandable interbody device. The location of the marker material can be on one or multiple locations on the expandable interbody device. The size of the one or more regions that include the marker material can be the same or different. The marker material can be spaced at defined distances from one another to form ruler-like markings on the expandable interbody device to facilitate in the positioning of the expandable interbody device in a treatment area.

The expandable interbody device can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

The expandable interbody device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the expandable interbody device. As defined herein, a “micro-structure” is a structure that has at least one dimension (e.g., average width, average diameter, average height, average length, average depth, etc.) that is no more than about 2 mm, and typically no more than about 1 mm. As can be appreciated, when the expandable interbody device includes one or more surface structures, 1) all the surface structures can be micro-structures, 2) all the surface structures can be non-micro-structures, or 3) a portion of the surface structures can be micro-structures and a portion can be non-micro-structures. Non-limiting examples of structures that can be formed on the expandable interbody devices are illustrated in United States Patent Publication Nos. 2004/0093076 and 2004/0093077, which are incorporated herein by reference.

In still yet another and/or alternative non-limiting aspect of the present disclosure, there is provided a near net process for a body or other metal component of the expandable interbody device. In one non-limiting embodiment of the disclosure, there is provided a method of powder pressing materials and increasing the strength post sintering by imparting additional cold work. In one non-limiting embodiment, the green part is pressed and then sintered. Thereafter, the sintered part is again pressed to increase its mechanical strength by imparting cold work into the pressed and sintered part. Generally, the temperature during the pressing process after the sintering process is 20-100° C. (and all values and ranges therebetween), typically 20-80° C., and more typically 20-40° C. As defined herein, cold working occurs at a temperature of no more than 150° C. (e.g., 10-150° C. and all values and ranges therebetween). The change in the shape of the repressed post-sintered part needs to be determined so the final part (pressed, sintered and re-pressed) meets the dimensional requirements of the final formed part. For a Mo47.5Re alloy, MoRe alloy, ReW alloy, molybdenum alloy, tungsten alloy, rhenium alloy, other type of refractory metal alloy, or TWIP alloy formed of a high titanium content, a prepress pressure of 1-300 tsi (1 ton per square inch) (and all values and ranges therebetween) can be used followed by a sintering process of at least 1600° C. (e.g., 1600-2600° C. and all values and ranges therebetween) and a post sintering press at a pressure of 1-300 tsi (and all values and ranges therebetween) at a temperature of at least 20° C. (e.g., 20-100° C. and all values and ranges therebetween; 20-40° C., etc.). There is also provided a process of increasing the mechanical strength of a pressed metal part by repressing the post-sintered part to add additional cold work into the material, thereby increasing its mechanical strength. There is also provided a process of powder pressing to a near net or final part using metal powder. In one non-limiting embodiment, the metal powder used to form the near net or final part includes a minimum of 40% rhenium by weight and at least 30% molybdenum, and the remainder can optionally include one or more elements of tungsten, tantalum, zirconium, iridium, titanium, bismuth, and yttrium. In another non-limiting embodiment, the metal powder used to form the near net or final part includes 20-80 wt. % rhenium (and all values and ranges therebetween), 20-80 wt. % molybdenum (and all values and ranges therebetween), and optionally one or more elements of tungsten, tantalum, zirconium, iridium, titanium, bismuth, and yttrium. In another non-limiting embodiment, the metal powder used to form the near net or final part includes tungsten (20-60 wt. % and all values and ranges therebetween), rhenium (20-80 wt. % and all values and ranges therebetween) and one or more other elements 0-5 wt. % (and all values and ranges therebetween). In another non-limiting embodiment, the metal powder used to form the near net or final part includes tungsten (20-80 wt. % and all values and ranges therebetween), rhenium (20-80 wt. % and all values and ranges therebetween), molybdenum (0-15 wt. % and all values and ranges therebetween), and one or more other elements 0-5 wt. % (and all values and ranges therebetween). In another non-limiting embodiment, the metal powder used to form the near net or final part includes tungsten (20-80 wt. % and all values and ranges therebetween), copper (1-30 wt. % and all values and ranges therebetween), and one or more other elements 0-5 wt. % (and all values and ranges therebetween). In another non-limiting embodiment, the metal powder used to form the near net or final part includes a titanium alloy or a cobalt alloy. The ductility of the refractory metal alloy measured as % reduction in area can increase and yield and ultimate tensile strength can increase.

In accordance with another and/or alternative non-limiting aspect of the present disclosure, there is provide a medical device that can be form by one or more manufacturing processes. These manufacturing processes can include, but are not limited to, laser cutting, etching, annealing, drawing, pilgering, electroplating, electro-polishing, machining, plasma coating, 3D printed coatings, 3D printing, chemical vapor deposition, chemical polishing, cleaning, pickling, ion beam deposition or implantation, sputter coating, vacuum deposition, etc. In one non-limiting embodiment, at least a portion or all of the medical device is formed by a 3D printing process.

In one non-limiting object of the present disclosure, there is provided an expandable interbody device that can be used as a prosthesis during spinal surgery.

In another and/or alternative non-limiting object of the disclosure, there is provided an expandable interbody device that is configured to be inserted into the space between spinal disks to provide stability. The expandable interbody device can be introduced between vertebrae of a patient's spine (e.g., in the disk space between adjacent vertebrae) for fixation with bone to immobilize the joint as part of a surgical treatment.

In another and/or alternative non-limiting object of the disclosure, there is provided an expandable interbody device that is configured to vertically expand on the first and/or second sides along a longitudinal length of the expandable interbody device.

In another and/or alternative non-limiting object of the disclosure, there is provided an expandable interbody device that can a) be independently vertically expanded along a first side while the second side is not vertically expanded; b) be independently vertically expanded along a second side while the first side is not vertically expanded; c) be vertically expanded the same amount along both the first and second sides; and/or d) be vertically expanded along the first side which is different from the vertical expansion along the second side.

In another and/or alternative non-limiting object of the disclosure, there is provided an expandable interbody device wherein the vertical expansion of the first and second sides can a) be the same amount for both the first and second sides, b) be a different amount for the first and second sides, c) occur at the same time for the first and second sides, and/or d) occur at different times for the first and second sides.

In another and/or alternative non-limiting object of the disclosure, there is provided an expandable interbody device that is configured to vertically expand both on the first and second sides along a longitudinal length of the expandable interbody device, and the expandable interbody device includes first and second drive arrangements wherein the first drive arrangement is configured to cause the first side of the expandable interbody device to expand vertically, and wherein the second drive arrangement is configured to cause the second side of the expandable interbody device to expand vertically.

In another and/or alternative non-limiting object of the disclosure, there is provided an expandable interbody device wherein the first and second drive arrangements can be operated independently from one another.

In another and/or alternative non-limiting object of the disclosure, there is provided an expandable interbody device wherein each drive arrangement includes at least one linkage, and a slide block.

In another and/or alternative non-limiting object of the disclosure, there is provided an expandable interbody device wherein a drive screw is configured to cause one or more of the slide blocks of a drive arrangement to move along a longitudinal axis of the expandable interbody device when the drive screw is rotated.

In another and/or alternative non-limiting object of the disclosure, there is provided an expandable interbody device wherein the drive screw is configured to cause the first and second slide blocks of a drive arrangement to move along a longitudinal axis of the expandable interbody device when the drive screw is rotated, and wherein the first slide block moves along a longitudinal axis of the expandable interbody device in an opposite direction from movement of the second slide block along a longitudinal axis of the expandable interbody device when the drive screw is rotated.

In another and/or alternative non-limiting object of the disclosure, there is provided an expandable interbody device wherein the expandable interbody device includes a main housing or drive block or core, top and bottom endplates, and one or more drive arrangements, and wherein each drive arrangement includes at least one linkage, and a slide block, and wherein one or more drive screws are used to cause the slide block to move relative to the main housing when the drive screw is rotated.

In another and/or alternative non-limiting object of the disclosure, there is provided an expandable interbody device wherein one or more of the drive screws is rotatable connected to the main housing or drive block or core and remains in position along a longitudinal axis of the expandable interbody and/or main housing or drive block or core when the drive screw is rotated.

In another and/or alternative non-limiting object of the disclosure, there is provided an expandable interbody device wherein each linkage has first and second end portions, and wherein the first end portion is rotatably or pivotally connected to a slide block and the second end portion is engaged with and/or is rotatably or pivotally connected to either the top or bottom endplates.

In another and/or alternative non-limiting object of the disclosure, there is provided an expandable interbody device includes a main housing or drive block or core, top and bottom endplates, and a first drive arrangement, and wherein the first drive arrangement causes the first side edge of each of the top and bottom endplates to move a same distance from the main housing or drive block or core when the drive screw for the first drive arrangement is rotated.

In another and/or alternative non-limiting object of the disclosure, there is provided an expandable interbody device includes a main housing or drive block or core, top and bottom endplates, and a second drive arrangement, and wherein the second drive arrangement causes the second side edge of each of the top and bottom endplates to move a same distance from the main housing or drive block or core when the drive screw for the second drive arrangement is rotated.

In another and/or alternative non-limiting object of the disclosure, there is provided an expandable interbody device includes the first and second drive arrangements that are independently operated from one another.

In another and/or alternative non-limiting object of the disclosure, there is provided an expandable interbody device includes a first drive arrangement that includes first and second slide blocks, and first and second sets of linkages on each of the slide blocks, wherein each set of linkages includes first and second linkages, and wherein a first drive screw threadedly engages the first and second slide blocks of the first drive arrangement, and wherein the first drive screw is simultaneously causes the first and second slide blocks to simultaneously move (e.g., simultaneously move toward one another, simultaneously move away from one another) when the first drive screw is rotated, and wherein the first drive screw moves 0-5% (and all values and ranges therebetween) along the longitudinal length of the main housing or the expandable interbody device during the rotation of the first drive screw.

In another and/or alternative non-limiting object of the disclosure, there is provided an expandable interbody device includes a second drive arrangement that includes first and second slide blocks, and first and second sets of linkages on each of the slide blocks, wherein each set of linkages includes first and second linkages, and wherein a second drive screw threadedly engages the first and second slide blocks of the second drive arrangement, and wherein the second drive screw is simultaneously causes the first and second slide blocks to simultaneously move (e.g., simultaneously move toward one another, simultaneously move away from one another) when the second drive screw is rotated, and wherein the second drive screw moves 0-5% (and all values and ranges therebetween) along the longitudinal length of the main housing or the expandable interbody device during the rotation of the second drive screw.

In another and/or alternative non-limiting object of the disclosure, the expandable interbody device optionally includes one or more graft windows, cavities and/or slots.

In another and/or alternative non-limiting object of the disclosure, the expandable interbody device optionally includes first and/or second endplates that include a micro-textured surface and/or one or more teeth.

In another and/or alternative non-limiting object of the disclosure, the expandable interbody device optionally includes first and second endplates that include planar top surfaces that lie within or closely within the same plane when the expandable interbody device is in the fully contracted position.

In another and/or alternative non-limiting object of the disclosure, one or more or all of the components of the expandable interbody device is partially or fully formed of a metal alloy selected from a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 awt. % rhenium.

In another and/or alternative non-limiting object of the disclosure, there is the provision of an expandable interbody device that is at least partially formed of a refractory alloy or a metal alloy that includes at least 15 atw. % rhenium.

In another and/or alternative non-limiting object of the disclosure, one or more portions of the outer surface of the expandable interbody device are coated with an enhancement layers such as chromium nitride (CrN), diamond-like carbon (DLC), titanium nitride (TiN), titanium oxynitride or titanium nitride oxide (TiNOx), zirconium nitride (ZrN), zirconium oxide ($ZrO_2$), zirconium oxynitride (ZrNxOy) [e.g., cubic ZrN:O, cubic $ZrO_2$:N, tetragonal $ZrO_2$:N, and monoclinic $ZrO_2$:N phase coatings], oxyzirconium-nitrogen-carbon (ZrNC), zirconium OxyCarbide (ZrOC), and combinations of such coatings.

In another and/or alternative non-limiting object of the disclosure, the expandable interbody device can optionally be partially or fully be coated with and/or include one or more agents.

In another and/or alternative non-limiting object of the disclosure, one or more portions of the expandable interbody device can include a marker material that facilitates enabling the expandable interbody device to be properly positioned in the treatment area.

Other objects, advantages, and novel features of the present invention will become apparent from the following detailed description of the invention when considered in conjunction with the accompanying drawings.

BRIEF DESCRIPTION OF THE DRAWINGS

The accompanying drawings, which are incorporated into and form a part of the specification, schematically illustrate one or more example implementations of the disclosed technology and, together with the general description given above and detailed description given below, serve to explain the principles of the disclosed subject matter, and wherein.

DETAILED DESCRIPTION OF NON-LIMITING EMBODIMENTS

Figure 1:
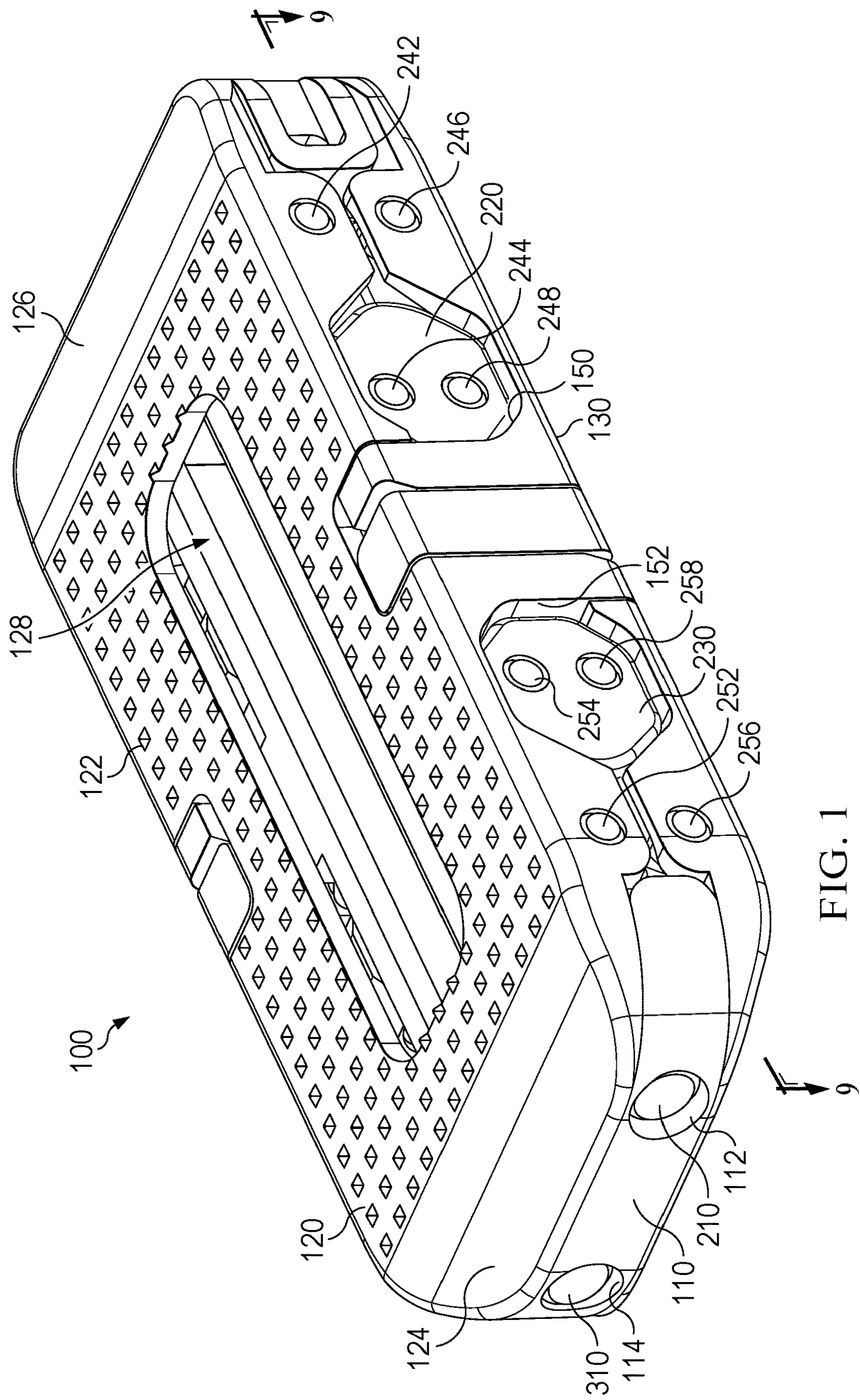
FIG. 1 is a front isometric view of the Expandable Medical Device in the closed or unexpanded position in accordance with the present disclosure.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

The devices, systems, and methods described herein include an expandable interbody device. The device includes linkages and sets of curved ramps that allow for simultaneous movement of the endplates relative to each other along specific paths to achieve a desired height and lordosis.

Referring now to FIGS. 1-15, there is illustrated an expandable interbody device 100 that can be used as an implant for spinal procedures.

The expandable interbody device 100 is illustrated as including a drive block or core 110, a top endplate 120, a bottom endplate 130, a first drive arrangement 200, and a second drive arrangement 300.

The drive block or core 110 extends about 80-100% (and all values and ranges therebetween) the longitudinal length of the expandable interbody device 100. In one non-limiting arrangement, the drive block or core 110 remains substantially stationary as the expandable interbody device 100 moves from the fully closed or collapsed position to the fully open or expanded position.

The first drive arrangement 200 includes a first drive screw 210, a first left side slide 220, a second left side slide 230, a first upper left side linkage 240, a second upper left side linkage 250, a first lower left side linkage 260 and a second lower left side linkage 270.

The second drive arrangement 300 includes a second drive screw 310, a first right side slide 320, a second right side slide 330, a first upper right-side linkage 340, a second upper right-side linkage 350, a first lower right-side linkage 360 and a second lower right-side linkage 370.

Each of the links are rotatably or pivotally connected and/or engaged to the side slide by a connection arrangement such as a pin. As illustrated in FIGS. 1, 2, 9 and 10, first left side slide 220 is connected and/or engaged (e.g., pivotally connected, pivotally engaged, etc.) to a lower portion of first upper left side linkage 240 and first lower left side linkage 260 via pins 246, 248, respectively. The upper portion of first upper left side linkage 240 and first lower left side linkage 260 is connected and/or engaged (e.g., pivotally connected, pivotally engaged, etc.) to the top endplate 120 and the bottom endplate 130, respectively via pins 242, 244. Second left side slide 230 is connected and/or engaged (e.g., pivotally connected, pivotally engaged, etc.) to a lower portion of second upper left side linkage 250 and second lower left side linkage 270 via pins 256, 258, respectively. The upper portion of second upper left side linkage 250 and second lower left side linkage 270 is connected and/or engaged (e.g., pivotally connected, pivotally engaged, etc.) to the top endplate 120 and the bottom endplate 130, respectively via pins 252, 254.

Referring again to FIGS. 1, 2, 9 and 10, first right-side slide 320 is connected and/or engaged (e.g., pivotally connected, pivotally engaged, etc.) to a lower portion of first upper right-side linkage 340 and first lower right-side linkage 360 via pins 346, 348, respectively. The upper portion of first upper right-side linkage 340 and first lower right-side linkage 360 is connected and/or engaged (e.g., pivotally connected, pivotally engaged, etc.) to the top endplate 120 and the bottom endplate 130, respectively via pins 342, 344. Second right side slide 330 is connected and/or engaged (e.g., pivotally connected, pivotally engaged, etc.) to a lower portion of second upper right-side linkage 350 and second lower right-side linkage 370 via pins 356, 358, respectively. The upper portion of second upper right-side linkage 350 and second lower right-side linkage 370 is connected and/or engaged (e.g., pivotally connected, pivotally engaged, etc.) to the top endplate 120 and the bottom endplate 130, respectively via pins 352, 354.

The drive block or core 110 includes screw cavities 112, 114 that extend along the longitudinal length of the drive block or core 110. Screw cavities 112, 114 are positioned generally parallel to one another and generally have the same shape and size; however, this is not required. Screw cavity 112 is configured to receive first drive screw 210 and screw cavity 114 is configured to receive second drive screw 310.

The rotation of the first drive screw 210 causes simultaneous movement of first and second left slides 220, 230. During rotation of first drive screw 210, first and second left slides 220, 230 move in opposition directions and away from one another along the longitudinal length of expandable interbody device 100 and drive block or core 110. First and second left slides 220, 230 are slidably positioned on the drive block or core 110 as first and second left slides 220, 230 move along the drive block or core 110. The first and second left slides 220, 230 can be slidably connected to the drive block or core 110.

Figure 14:
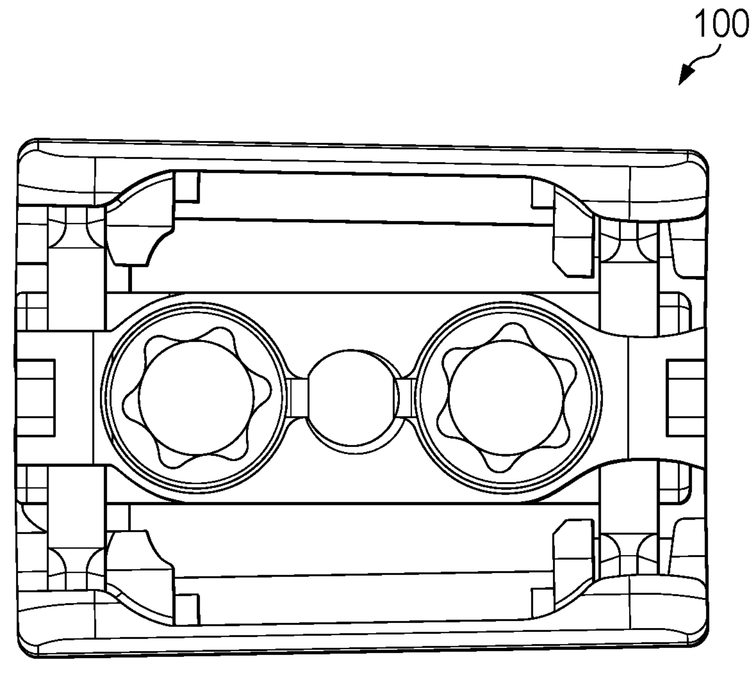
Figure 15:
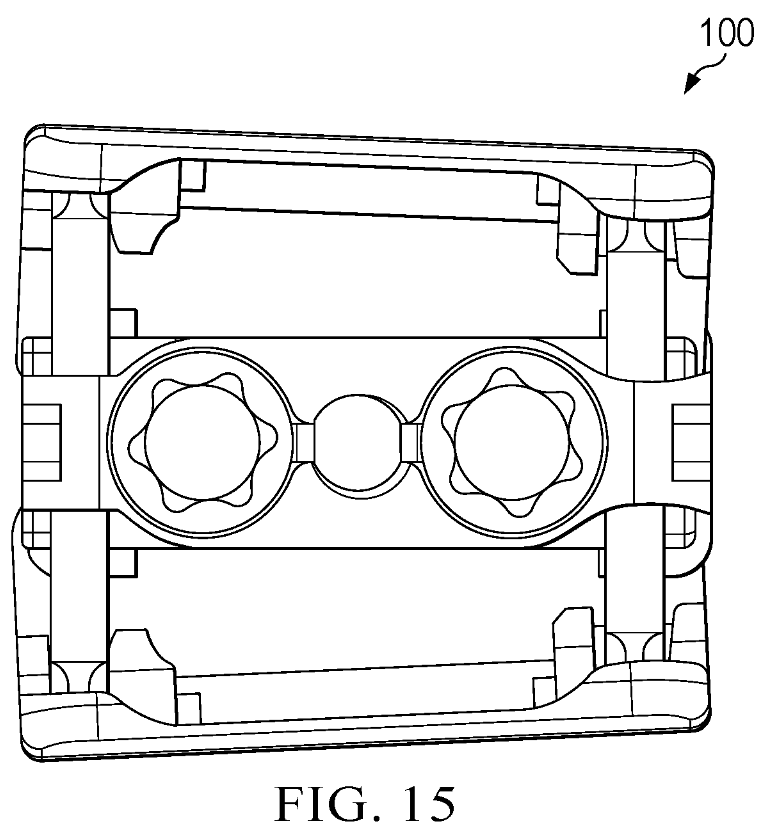

First and second left slides 220, 230 each include an opening 222, 232 wherein a portion of first drive screw 210 is inserted therein. Each opening 222, 232 can optionally be threaded to receive a threaded portion 212, 214 of first device screw 210 as illustrated in FIGS. 14 and 15. The first drive screw 210 can optionally include a non-slide region 216 that inhibits or prevents the longitudinal movement of first drive screw 210 when rotated. As illustrated in FIG. 14, non-slide region 216 is located between threaded portions 212, 214; however, this is not required. The non-slide region 216 is illustrated as being a threaded region; however, this is not required. The non-slide region 216 is located in mid-core region 116 that is configured to inhibit or prevent the non-slide region from longitudinally moving out of mid-core region 116 when first drive screw 210 is rotated. In one non-limiting arrangement, during the rotation of first drive screw 210, the drive screw 210 moves 0-5% (and all value and ranges therebetween) the longitudinal length of the drive block or core 110.

The rotation of the second drive screw 310 causes simultaneous movement of first and second right slides 320, 330. During rotation of second drive screw 310, first and second right slides 320, 330 move in opposition directions and away from one another along the longitudinal length of expandable interbody device 100 and drive block or core 110. First and second right slides 320, 330 are slidably positioned on drive block or core 110 as first and second right slides 320, 330 move along drive block or core 110. The first and second right slides 320, 330 can be slidably connected to the drive block or core 110.

First and second right slides 320, 330 each include an opening 322, 332 wherein a portion of second drive screw 310 is inserted therein. Each opening 322, 332 can optionally be threaded to receive a threaded portion 312, 314 of second device screw 310 as illustrated in FIGS. 14 and 15. The first drive screw 310 can optionally include a non-slide region 316 that inhibits or prevents the longitudinal movement of the first drive screw 210 when rotated. As illustrated in FIG. 14, the non-slide region 316 is located between threaded portions 312, 314; however, this is not required. The non-slide region 316 is illustrated as being a threaded region; however, this is not required. The non-slide region 316 is located in mid-core region 116 that is configured to inhibit or prevent the non-slide region from longitudinally moving out of the mid-core region 116 when the first drive screw 310 is rotated. In one non-limiting arrangement, during the rotation of second drive screw 310, the drive screw 310 moves 0-5% (and all value and ranges therebetween) the longitudinal length of the drive block or core 110.

Figure 2:
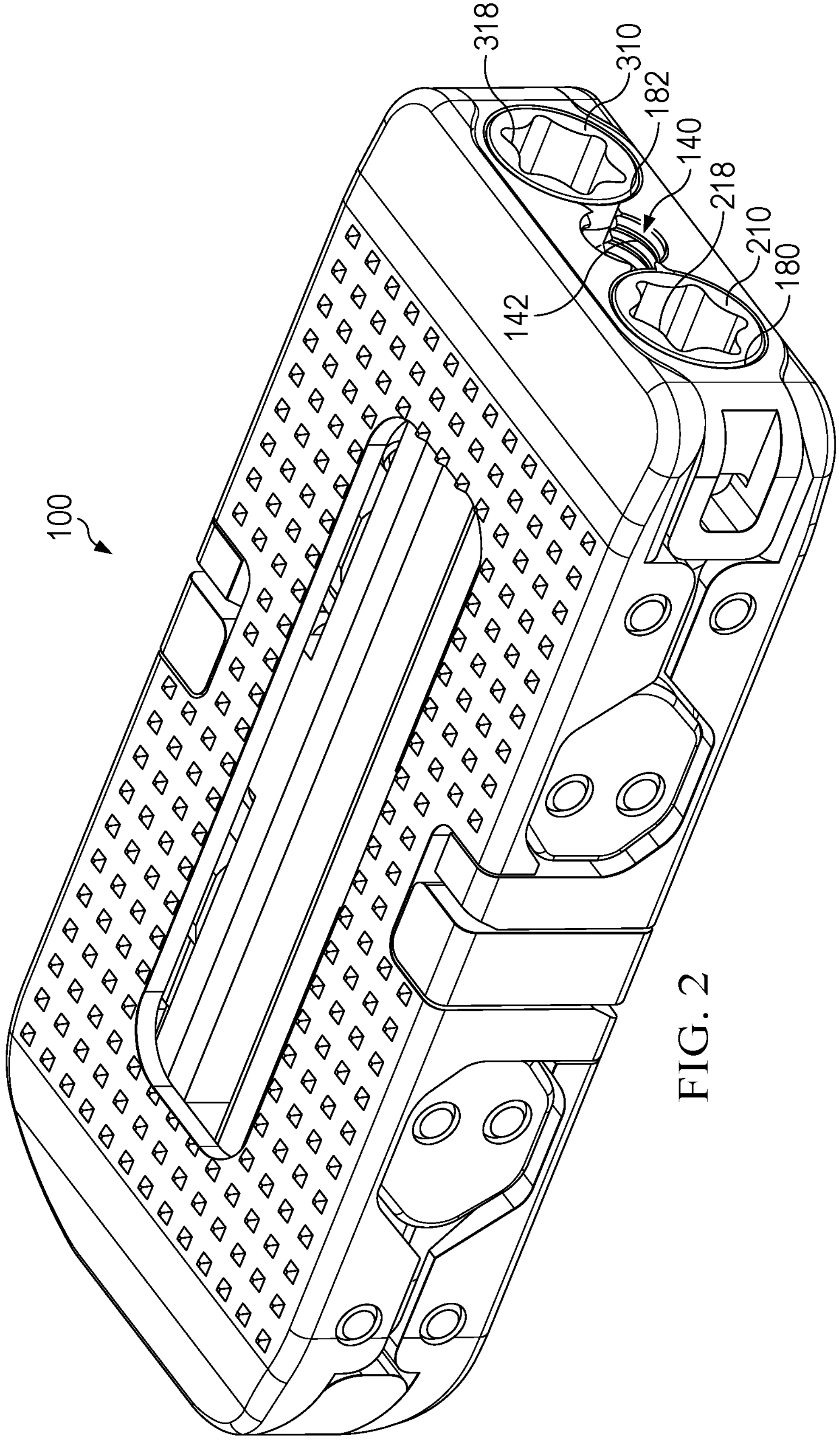
FIG. 2 is a rear isometric view of the Expandable Medical Device of FIG. 1.
Figure 10:
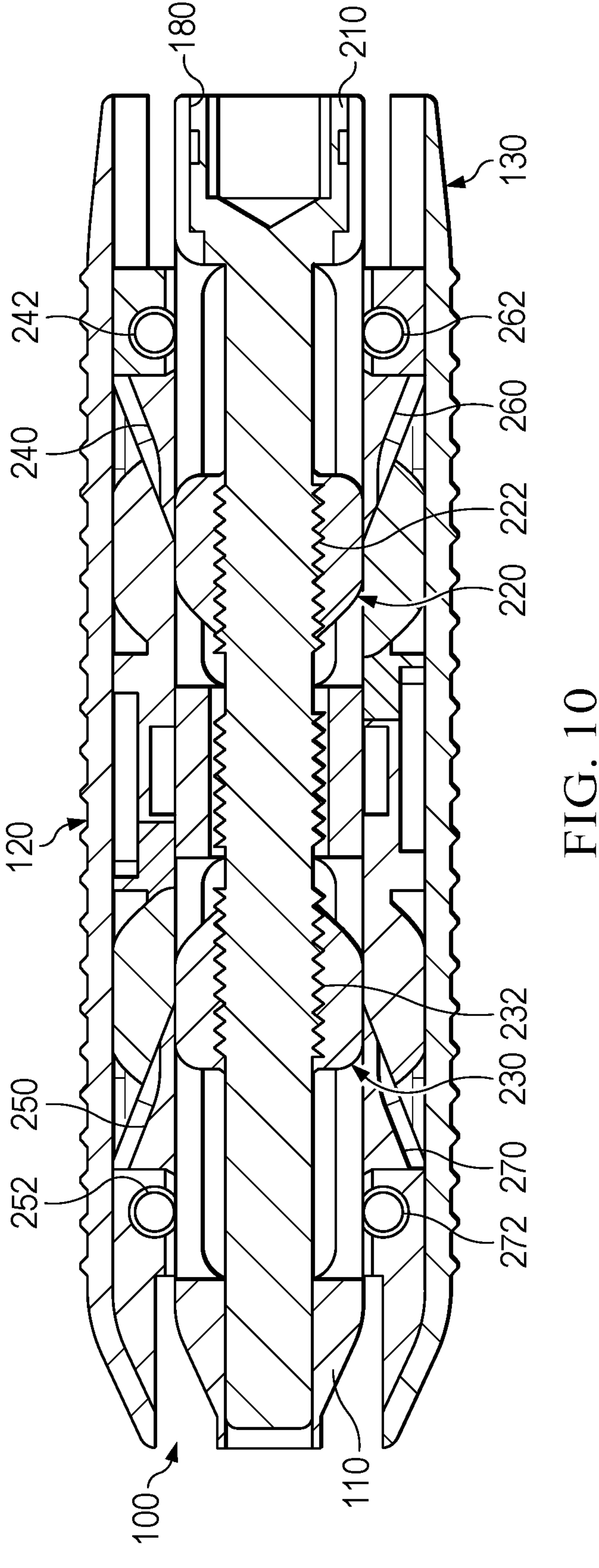
FIG. 10 is a cross-sectional view of the Expandable Medical Device along line 10-10 of FIG. 3.

The head portion of each of first and second drive screws 210, 310 can include a tool opening 218, 318 that is configured to releasably receive a tool, not shown. The tool can be configured to rotate first and/or second drive screws 210, 310 to cause the top and bottom endplates 120, 130 to move between the fully closed and fully expanded positions. Tool openings 218, 318 can have the same or different size and/or configuration. As illustrated in FIG. 2, tool openings 218, 318 have a star-shaped configuration which is the same size and shape; however, other shapes can be used (e.g., oval shape, polygonal shape, square shaped, triangular shape, etc.). As illustrated in FIG. 2, the head portion of first and second drive screws 210, 310 is partially or fully positioned in rear openings 180, 182, respectively of drive block or core 110. As illustrated in FIG. 10, the cross-sectional area of the rear openings 180, 182 decrease at a location that is spaced from the rear or distal end of the drive block or core 110.

The rear or distal end of drive block or core 110 includes a delivery opening 140 that is configured to receive an insertion tool (not shown). The insertion tool can be configured to be releasably connected to delivery opening 140. The insertion tool can be used by a user (e.g., surgeon, etc.) to insert expandable interbody device 100 into the treatment area. After expandable interbody device 100 is properly positioned in the treatment area (and optionally after expandable interbody device 100 has been expanded), the insertion tool can be removed from delivery opening 140. As illustrated in FIG. 2, delivery opening 140 includes a threaded region 142 that enable the insertion tool to be threadedly connected to the expandable interbody device 100. As illustrated in FIG. 2, the delivery opening 140 is positioned between rear openings 180, 182. As illustrates in FIG. 2, the cross-sectional area of the delivery opening 140 is smaller than rear openings 180, 182; however, this is not required.

The top surface of top and/or bottom endplates 120, 130 can optionally include a textured surface 122, 132 to facilitate in the gripping and/or bonding of expandable interbody device 100 to bone and/or tissue once expandable interbody device 100 inserted into the treatment area. The middle surface of first and second endplates 120, 130 has a generally planar or flat surface along 50-100% (and all values and ranges therebetween) of the longitudinal length of the endplates. The longitudinal length of the top surface of the top and bottom endplates is generally greater that the width of the endplates. Generally, the width of the endplates is 20-80% (and all values and ranges therebetween) of the longitudinal length of the endplates. As illustrated in FIG. 1, the plane of the top surface of top endplate 120 is generally parallel (e.g., ±5° and all values and ranges therebetween) to the plane of the top surface of bottom endplate 130 when expandable interbody device 100 is in the fully closed or unexpanded position.

The front and/or rear regions 124, 126 of top endplate 120 can optionally include a downwardly sloping surface (e.g., 5-30° and all values and ranges therebetween). Such downwardly sloping surfaces can optionally be absent textured surface 122. Front and/or rear regions 134, 136 of bottom endplate 130 can optionally include an upwardly sloping surface (e.g., 5-30° and all values and ranges therebetween). Such upwardly sloping surfaces can optionally be absent textured surface 132. The sloped surfaces on the front and/or rear regions on the top and/or bottom endplates 120, 130 (when used) facilitate in the insertion and/or positioning of expandable interbody device 100 in the treatment area.

Figure 3:
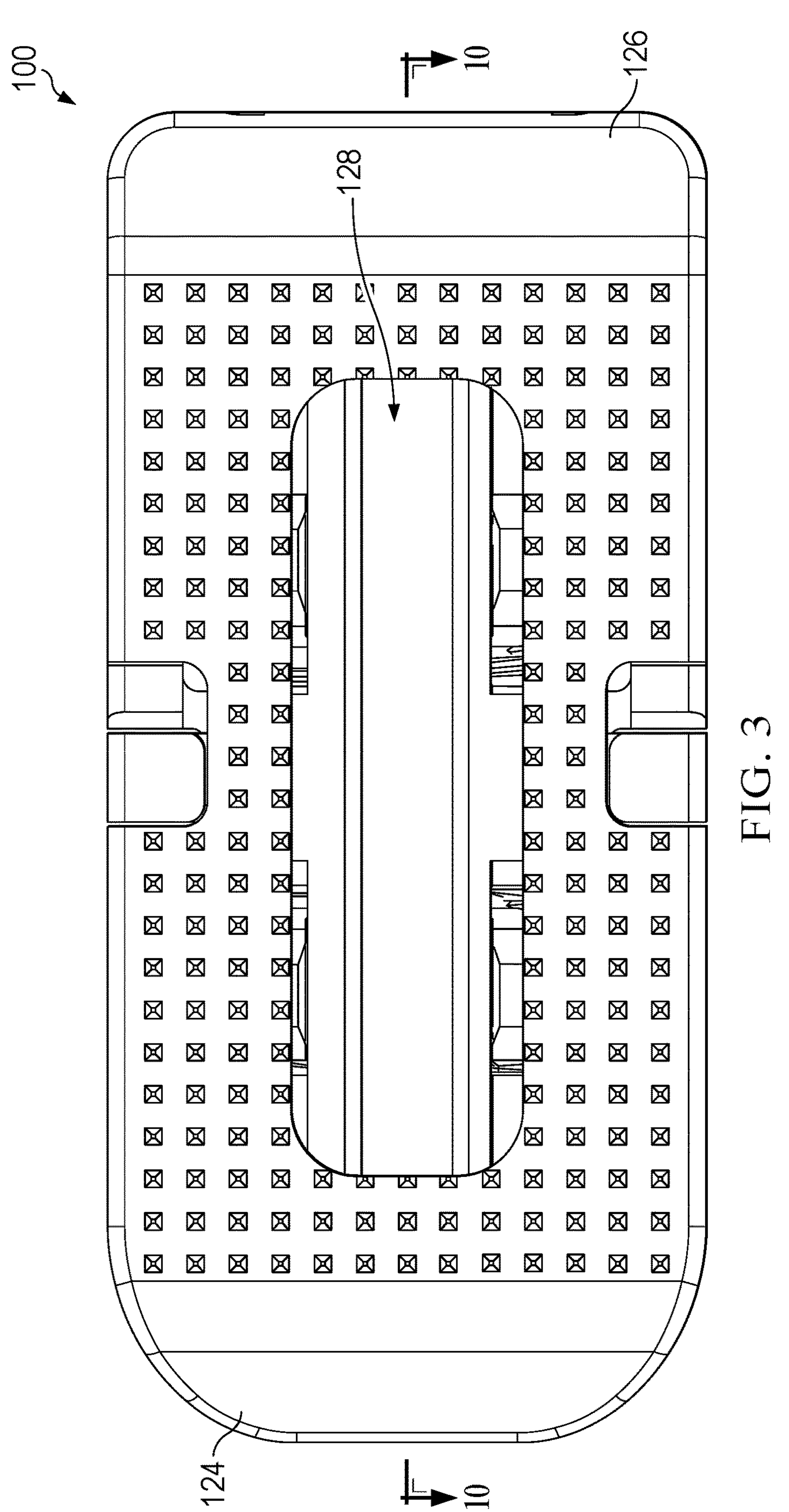
FIG. 3 is a top plan view of the Expandable Medical Device of FIG. 1.
Figure 4:
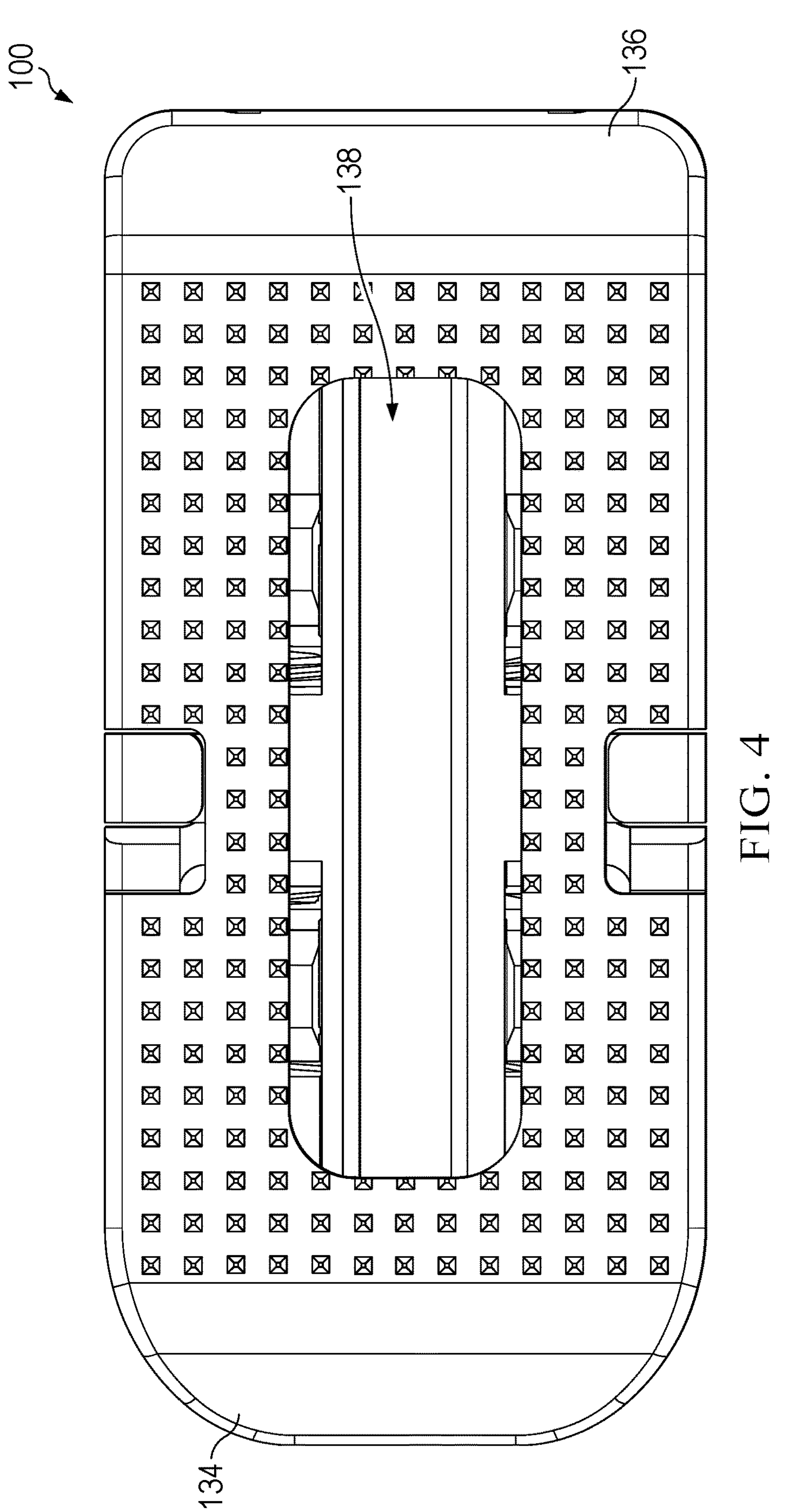
FIG. 4 is a bottom plan view of the Expandable Medical Device of FIG. 1.
Figure 9:
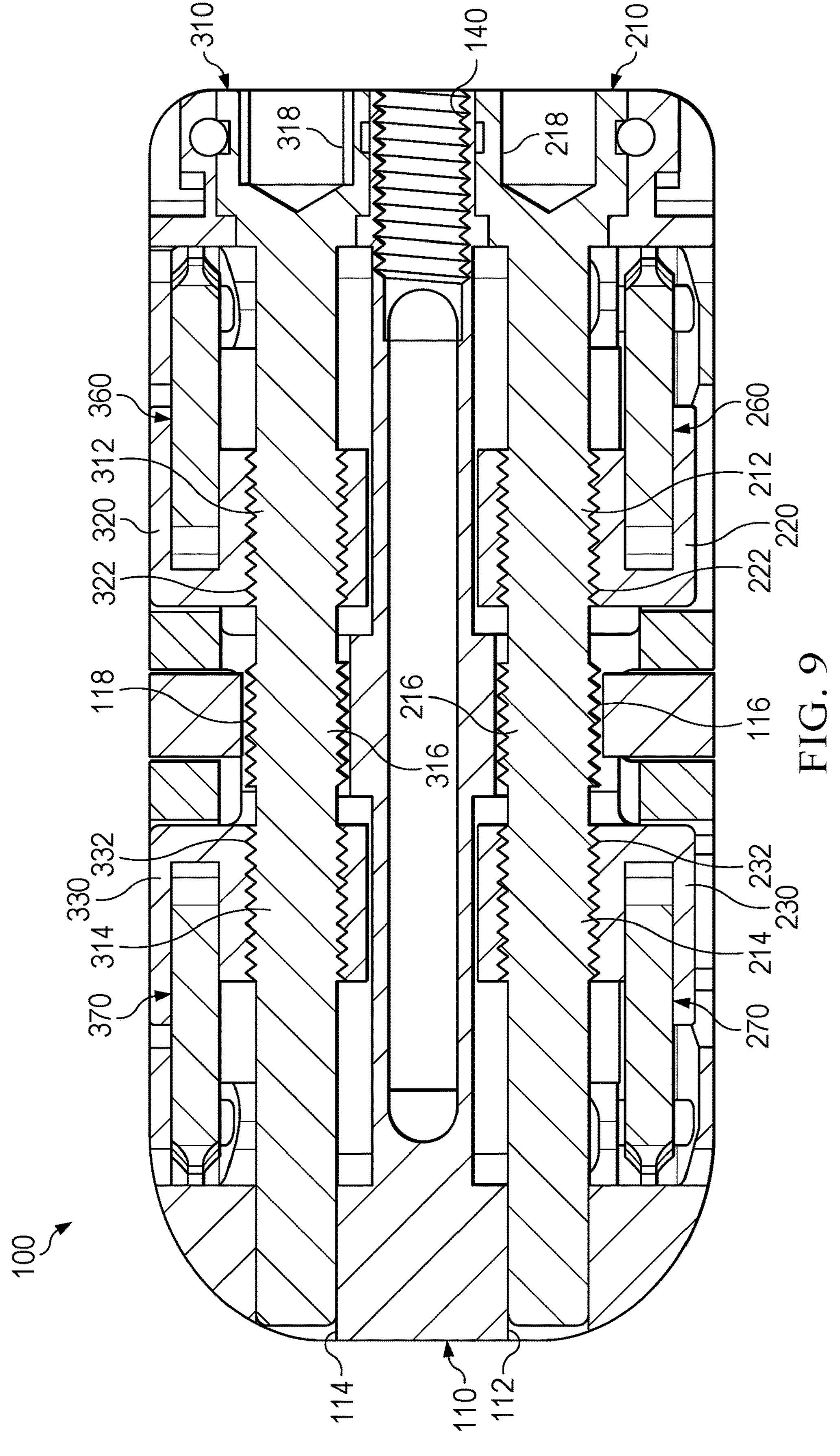
FIG. 9 is a cross-sectional view of the Expandable Medical Device along line 9-9 of FIG. 1.

Top and/or bottom endplates 120, 130 can optionally include a graft window 128, 138 to facilitate in the bonding of expandable interbody device 100 to bone and/or tissue once expandable interbody device 100 inserted into the treatment area. The size and shape of graft windows 128, 138 (when used), are non-limiting. As illustrated in FIGS. 3 and 4, graft windows 128, 138 have an oval shape and are generally the same size; however, this is not required. Graft windows 128, 138 (when used) constitute less than 50% (e.g., 10-49% and all values and ranges therebetween) of the top surface area of the endplates on which the graft window is present. The drive block or core 110 can optionally include an opening as illustrated in FIGS. 3, 4 and 9, and such opening in the drive block or core 110, when used, can be optionally aligned with graft windows 128, 138 when the expandable interbody device 100 is in the fully closed or collapsed position.

When top and bottom endplates 120, 130 are in the fully closed or non-expanded position as illustrated in FIG. 1, the sides of top and bottom endplates 120, 130 have a shape that forms a slide cavity 150, 152, 154, 156 that at least partially encircles (e.g., encircles 30-100% and all values and ranges therebetween) the outer side of the slide that is located in a respective slide cavity. As illustrated in FIGS. 1, 2, 5 and 6, the sides of top and bottom endplates 120, 130 have sloped surfaces that are configured to engage with a corresponding sloped surface on side slides 220, 230, 320, 330 when the left and/or right-side slides are caused to move when one or both drive screws 210, 310 are rotated. In one non-limiting arrangement, when the expandable interbody device 100 is in the fully closed or collapsed position, and drive screw 210 is initially rotated to cause first and second left side slides 220, 230 to begin moving away from one another, the angled surface on the first and second left side slides 220, 230 eventually engages the sloped surfaces on the slide cavity 150, 152 to facilitate in causes initially separation of the left side of top and bottom endplates 120, 130. As the drive screw 210 is continued to be rotated, the left side of top and bottom endplates 120, 130 disengage from the first and second left side slides 220, 230 as the left side of top and bottom endplates 120, 130 continue to separate from one another. Likewise, when the expandable interbody device 100 is in the fully closed or collapsed position, and drive screw 310 is initially rotated to cause first and second right side slides 320, 330 to begin moving away from one another, the angled surface on the first and second right side slides 320, 330 eventually engages the sloped surfaces on the slide cavity 154, 156 to facilitate in causes initially separation of the right side of top and bottom endplates 120, 130. As the drive screw 210 is continued to be rotated, the right side of top and bottom endplates 120, 130 disengage from the first and second right side slides 320, 330 as the right side of top and bottom endplates 120, 130 continue to separate from one another.

FIGS. 1-10 are various views of the expandable interbody device 100 wherein top and bottom endplates 120, 130 are in the fully closed or non-expanded position. FIGS. 11-15 illustrated the expandable interbody device 100 wherein top and bottom endplates 120, 130 are in various open or expanded positions.

Expandable interbody device 100 is configured such that the left side of expandable interbody device 100 can be oriented in various positions from the fully closed or non-expanded position to the fully open or fully-expanded position while the right side of expandable interbody device 100 can be oriented in various positions from the fully closed or non-expanded position to the fully open or fully-expanded position. The position of the expanded position of the left and right sides can be the same or different. The opening and/or closing of the left side of the interbody device 100 can be independent of the opening and/or closing of the right side of the interbody device 100.

Figure 11:
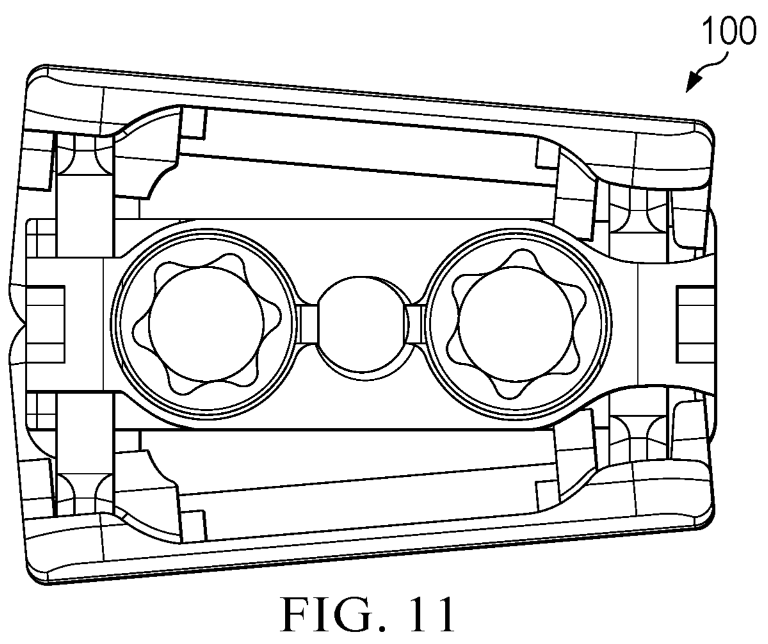
FIGS. 11-15 are front end plan views of the Expandable Medical Device of FIG. 1 illustrating various positions of the top endplate and bottom endplate.
Figure 12:
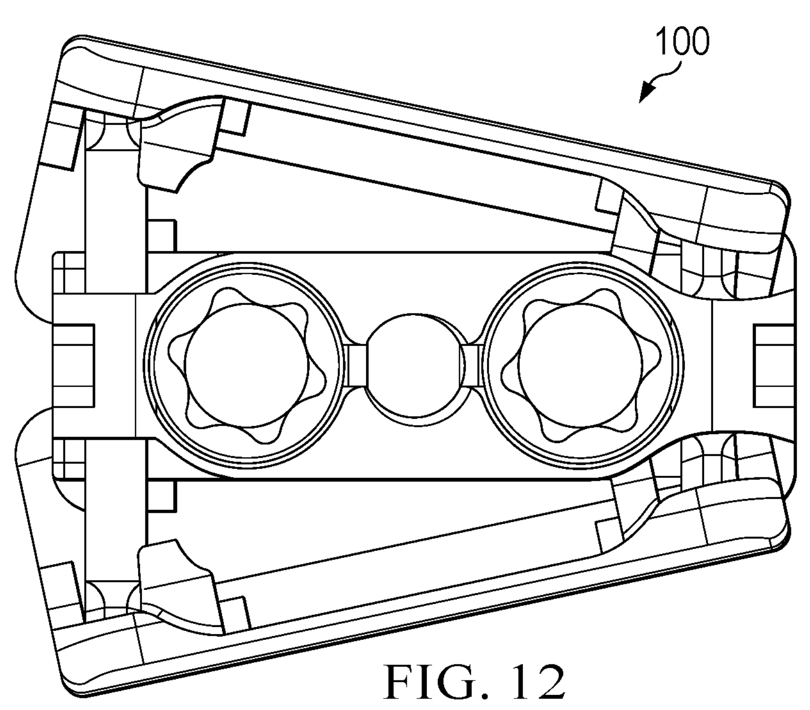
Figure 13:
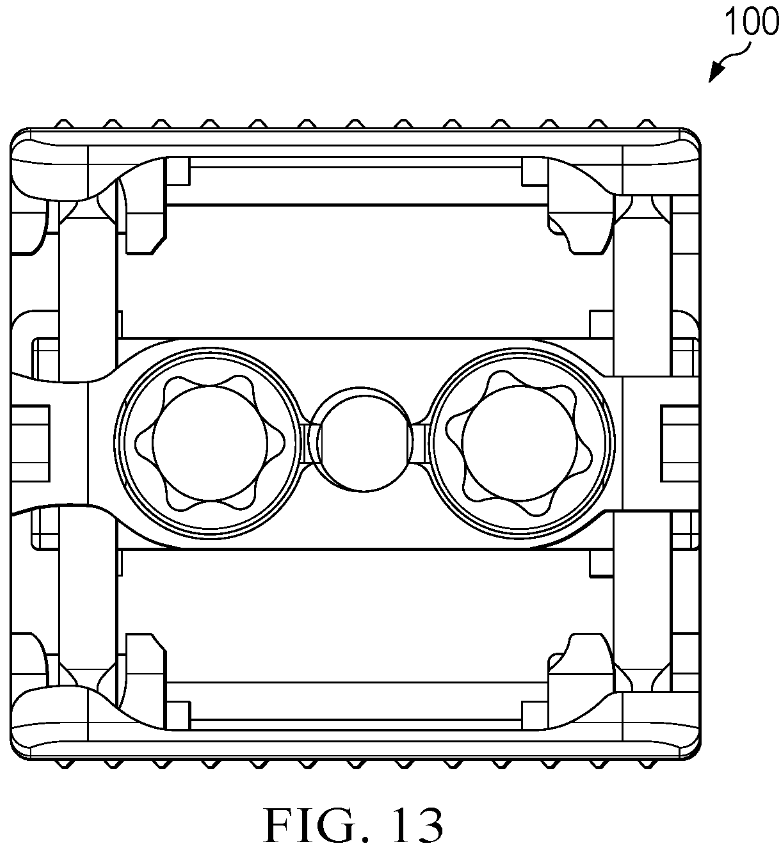

As illustrated in FIG. 11, both the left and right sides of expandable interbody device 100 are slightly expanded (e.g., expanded 10.001-25% and all values and ranges therebetween of the fully expanded position) the same amount. FIG. 12 illustrates the left side of expandable interbody device 100 moderately expanded (e.g., expanded 30-60% and all values and ranges therebetween of the fully expanded position) and the right side of expandable interbody device 100 unexpanded or very slightly expanded (e.g., expanded 0-10% and all values and ranges therebetween of the fully expanded position). FIG. 14 illustrates the left side and right side of expandable interbody device 100 moderately expanded (e.g., expanded 30-60% and all values and ranges therebetween of the fully expanded position). FIG. 15 illustrates the left side of expandable interbody device 100 substantially or full expanded (e.g., expanded 80-100% and all values and ranges therebetween of the fully expanded position) and the right side of expandable interbody device 100 moderately expanded (e.g., expanded 30-60% and all values and ranges therebetween of the fully expanded position). FIG. 13 illustrates the left and right side of expandable interbody device 100 substantially or full expanded (e.g., expanded 80-100% and all values and ranges therebetween of the fully expanded position). As can be appreciated, the left side of expandable interbody device 100 can be 0-100% (e.g., expanded 80-100% and all values and ranges therebetween of the fully expanded position), and the right side of expandable interbody device 100 can be 0-100% (e.g., expanded 80-100% and all values and ranges therebetween of the fully expanded position).

Figure 5:
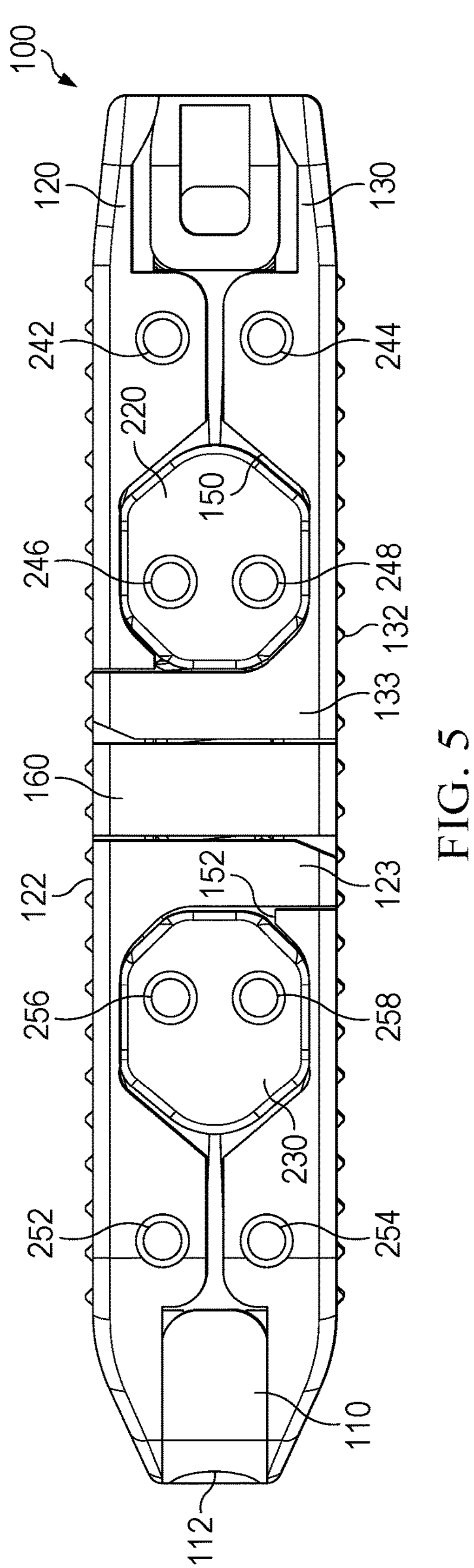
FIG. 5 is a first side view of the Expandable Medical Device of FIG. 1.
Figure 6:
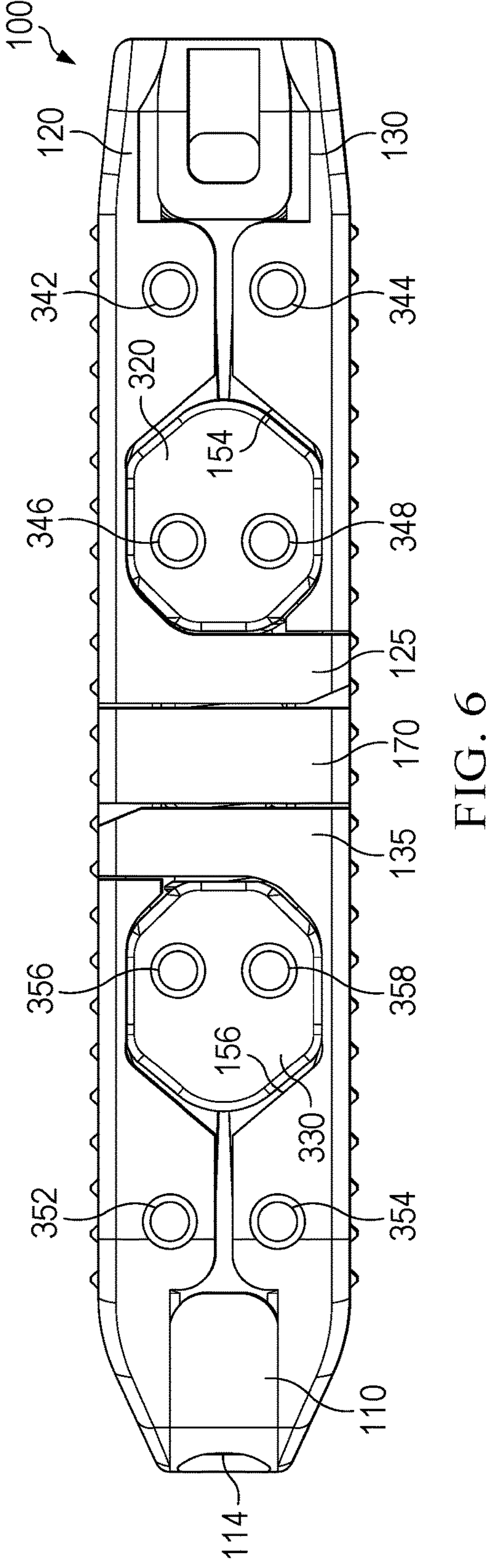
FIG. 6 is an opposite side view of the Expandable Medical Device of FIG. 1.
Figure 7:
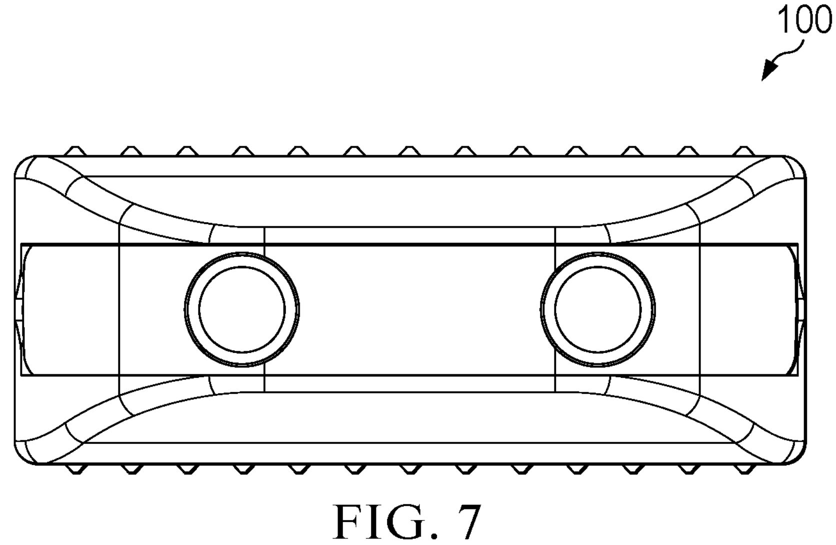
FIG. 7 is a front-end plan view of the Expandable Medical Device of FIG. 1.
Figure 8:
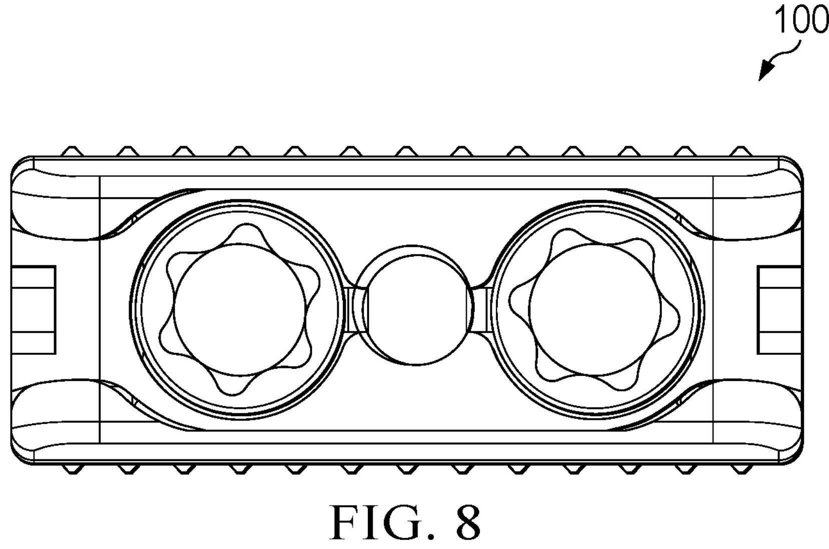
FIG. 8 is a rear end plan view of the Expandable Medical Device of FIG. 1.

The drive block or core 110 can optionally include side guides 160, 170 to facilitate in maintaining the longitudinal position of top and bottom endplates 120, 130 relative to drive block or core 110 as the endplates move between the fully closed and fully expanded positions. Top endplate 120 can include side flanges 123, 125 on the sides of top endplate 120. Bottom endplate 130 can include side flanges 133, 135 on the sides of bottom endplate 120. These side flanges are configured to move alongside guides 160, 170 as the endplates move between the fully closed and fully expanded positions. As illustrated in FIGS. 5 and 6, side flange 123 is located on the left side of expandable interbody device 100 and forwardly of side guide 160, and side flange 125 is located on the right side of expandable interbody device 100 and rearwardly of side guides 170. As also illustrated in FIGS. 5 and 6, side flange 133 is located on the left side of expandable interbody device 100 and rearwardly of side guide 160, and side flange 135 is located on the right side of expandable interbody device 100 and forwardly of side guides 170. Such an orientation of the side guides and side flanges facilitates in maintaining the longitudinal position of the top and bottom endplates 120, 130 relative to drive block or core 110 as the endplates move between the fully closed and fully expanded positions.

Figure 16:
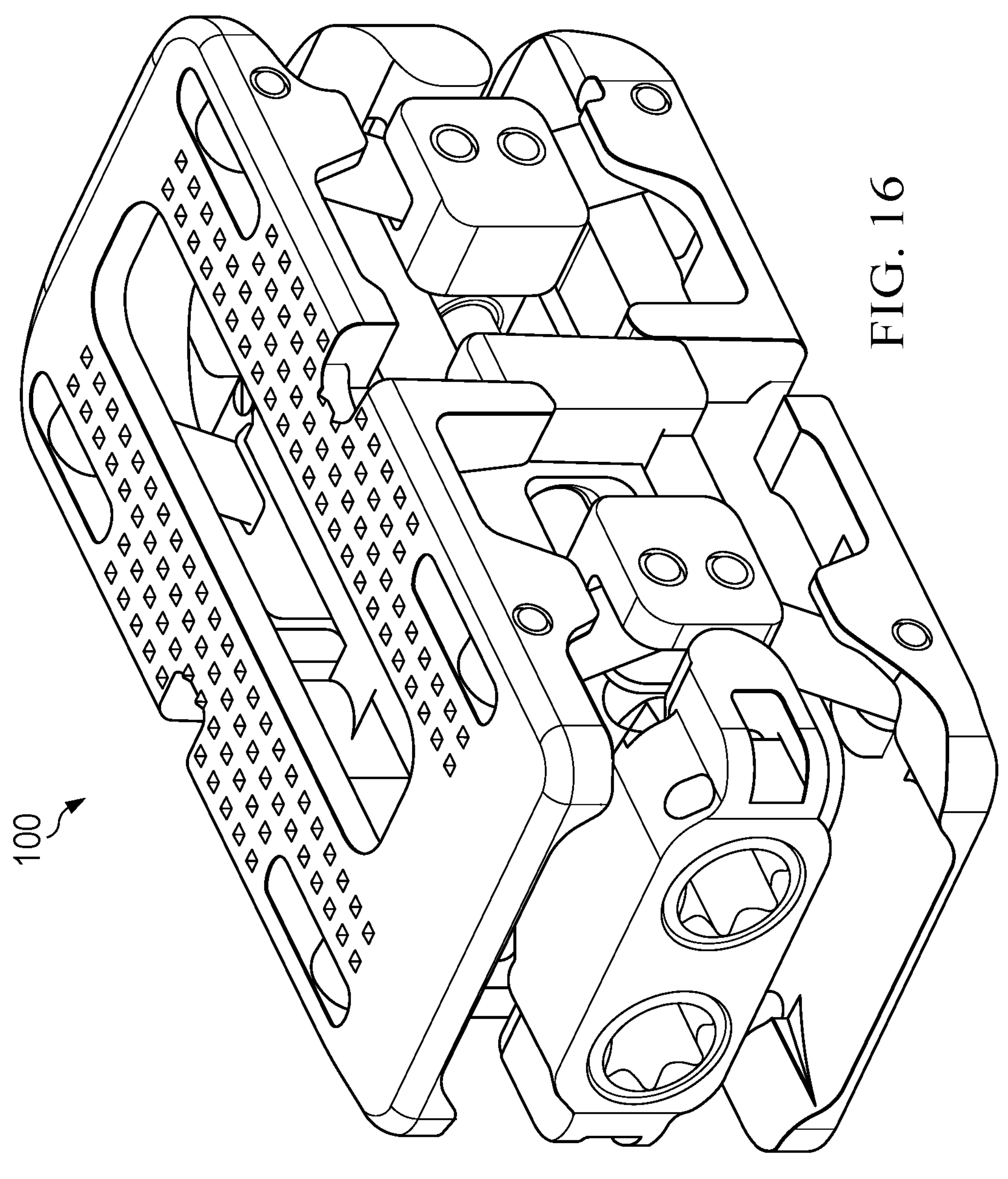
FIG. 16 is an isometric front elevation view of another non-limiting embodiment of the Expandable Medical Device wherein the top and bottom endplates are in the fully expanded position.
Figure 17:
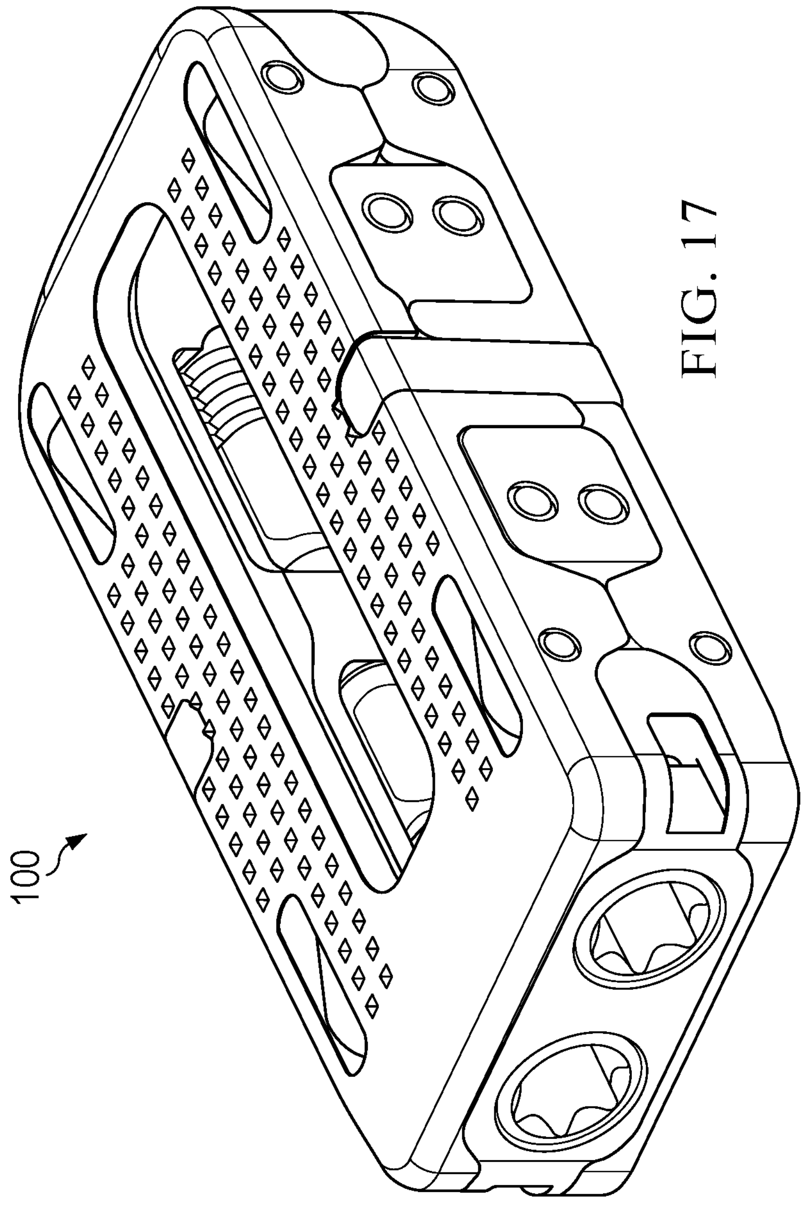
FIG. 17 is an isometric front elevation view of the Expandable Medical Device of FIG. 16 wherein the top and bottom endplates are in the fully collapsed position.
Figure 18:
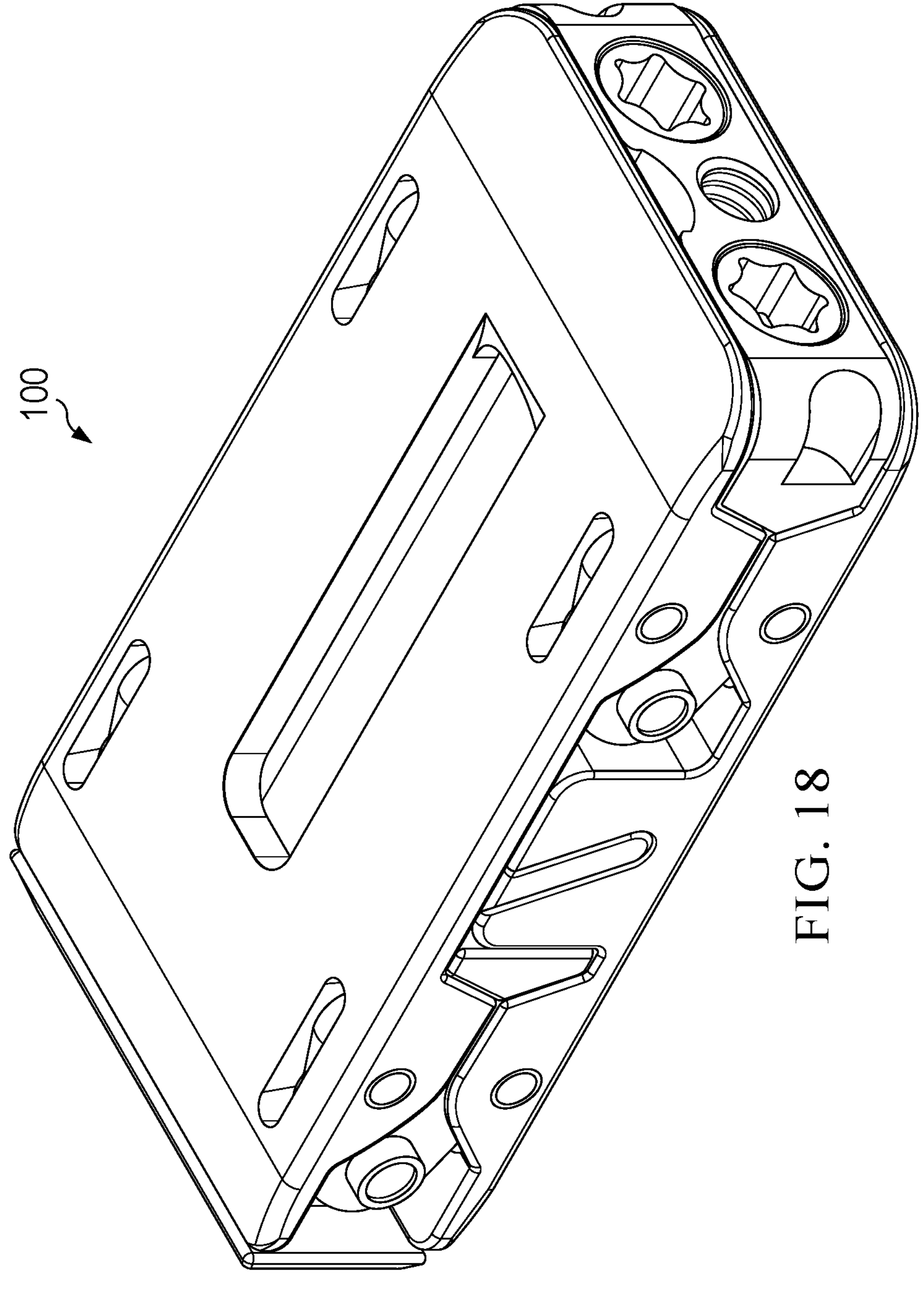
FIG. 18 is a rear isometric view of yet another non-limiting embodiment of an Expandable Medical Device in the closed or unexpanded position in accordance with the present disclosure.
Figure 19:
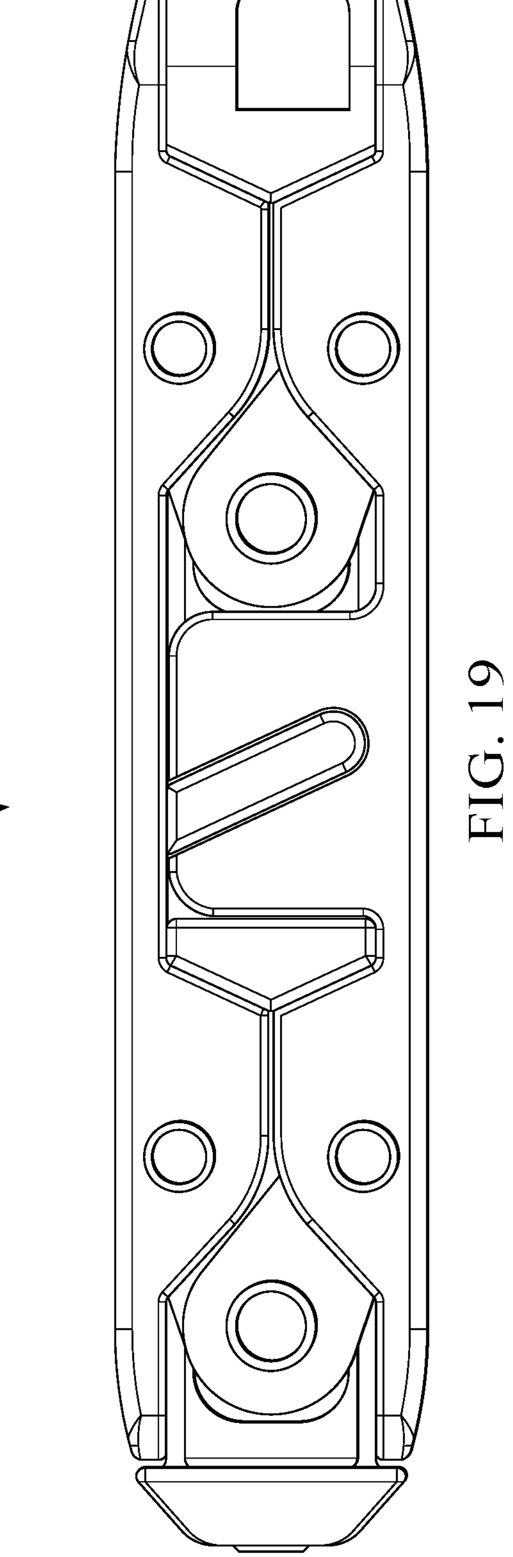
FIG. 19 is a first side view of the Expandable Medical Device of FIG. 18.

Referring now to FIGS. 16 and 17, there is illustrated another non-limiting embodiment of the expandable interbody device 100 in accordance with the present disclosure. The components and operation of the expandable interbody device 100 illustrated in FIGS. 16-17 are the same as illustrated and described above with respect to the expandable interbody device 100 illustrated in FIGS. 1-15, except that the expandable interbody device 100 illustrated in FIGS. 16-17 a) includes additional openings in the top and bottom endplates 120, 130 to allow for access to or movement of the linkages relative to the top and bottom endplates 120, 130, b) has modified side guide arrangement that are used to facilitate in maintaining the longitudinal position of top and bottom endplates 120, 130 relative to drive block or core 110 as the endplates move between the fully closed and fully expanded positions, c) has a modified shape of the top and bottom endplates 120, 130, d) has a modified shape of the side slides, e) is absent a delivery opening 140, and f) has a different top surface texture configuration on the top surface of the top and bottom endplates 120, 130.

Now referring to FIGS. 18-21, there is illustrated yet another non-limiting embodiment of the expandable interbody device 100 in accordance with the present disclosure. The components and operation of the expandable interbody device 100 illustrated in FIGS. 18-21 are the same as illustrated in FIGS. 1-15 and 16-17, except that the expandable interbody device 100 illustrated in FIGS. 18-21 has modified side guide arrangements that are used to facilitate in controlling the longitudinal movement of the drive block or core 110 relative to the top and bottom endplates 120, 130 as the top and bottom endplates 120, 130 move between the fully closed and fully expanded positions, or vice versa. Specifically, the modified side guide arrangements disclosed in FIGS. 18-21 allow the drive block or core 110 to be slightly repositioned relative to the top and bottom endplates 120, 130 when device 100 is in its fully expanded position. As illustrated in FIG. 1, 2-20% (and all values and ranges therebetween) of the longitudinal length of the drive block or core 110 is positioned forwardly of the front end of the top and bottom endplates 120, 130 when the top and bottom endplates 120, 130 move to the fully expanded position. Also, the rear end of the drive block or core 110 is positioned forwardly of the rear end of the top and bottom endplates 120, 130 when the top and bottom endplates 120, 130 move to the fully expanded position.

Figure 20:
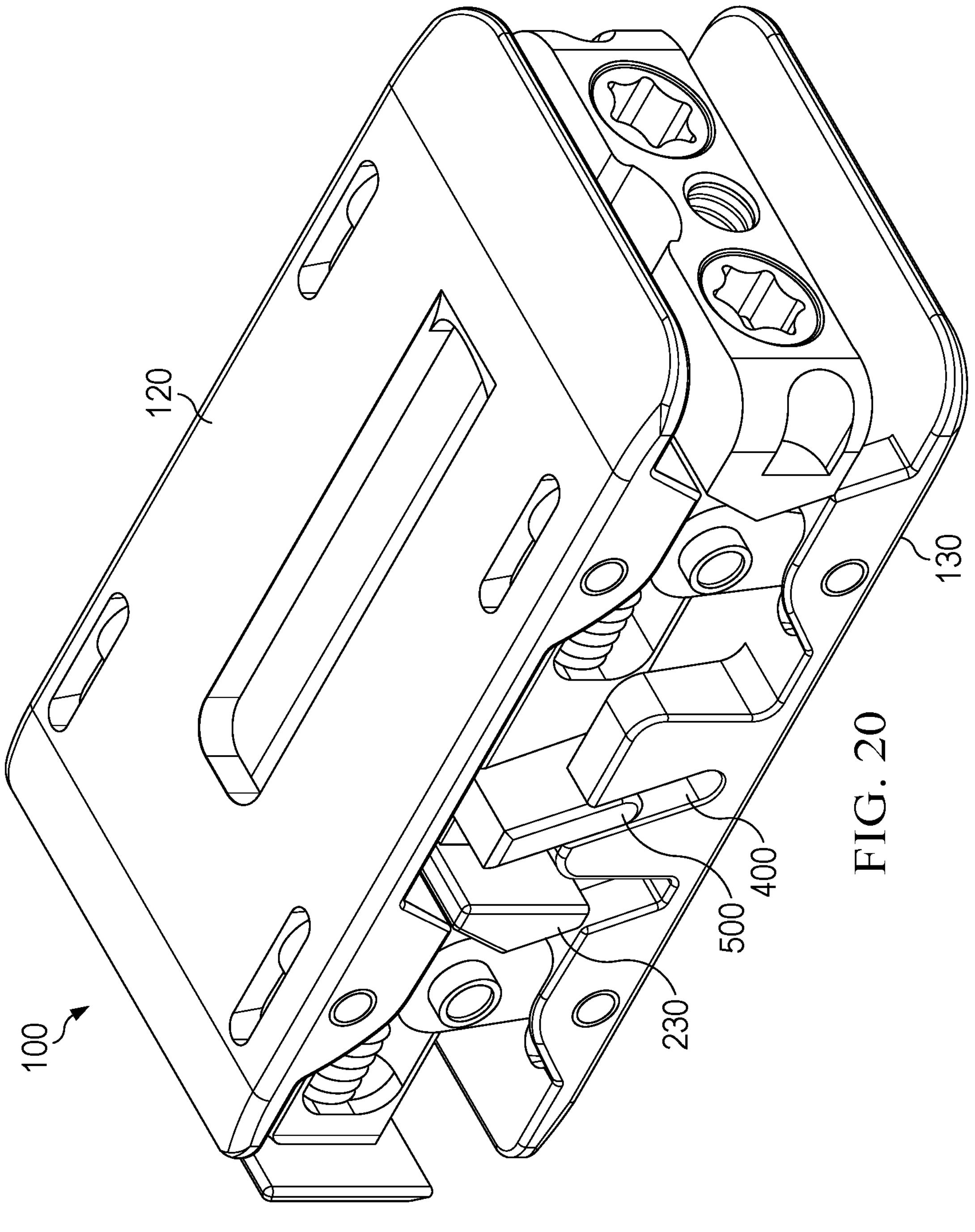
FIG. 20 is a rear isometric view of the Expandable Medical Device of FIG. 18 wherein top and bottom endplates are in an expanded position.
Figure 21:
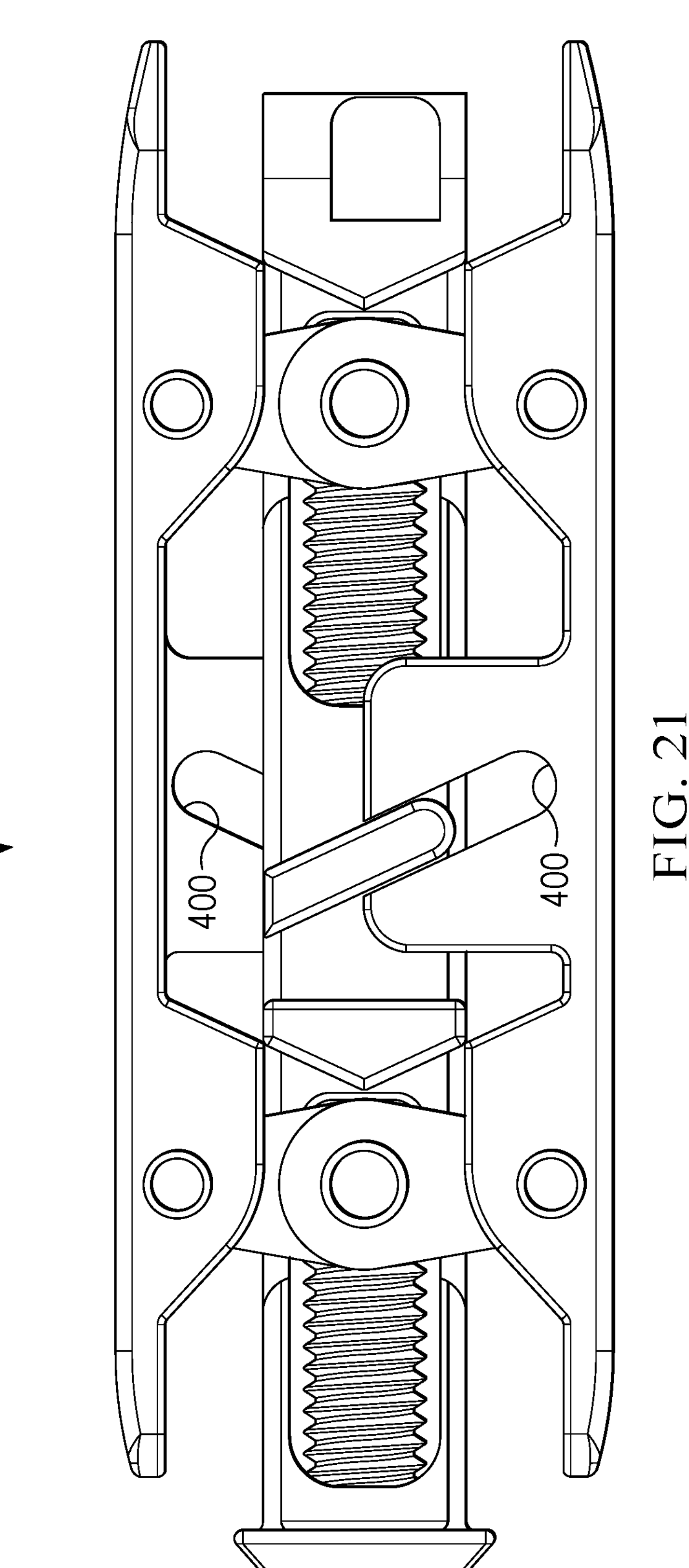
FIG. 21 is a first side view of the Expandable Medical Device of FIG. 20.

The drive block or core 110 includes the modified guide arrangements that are configured to move within one or more slots formed on top endplate 120 and/or bottom endplate 130. As illustrated in FIG. 20, the top and bottom endplates 120, 130 of the expandable interbody device 100 include an angular side guide arrangement 400 that causes the longitudinal movement of the drive block or core 110 relative to the top and bottom endplates 120, 130 as the top and bottom endplates 120, 130 move between the fully closed and fully expanded positions, or vice versa. The angle of the angular side guide arrangement 400 is about 10-45° (and all values and ranges therebetween). The angular side guide arrangement 400 is on one side of the expandable interbody device 100 is configured to angle forwardly toward the front end of the expandable interbody device 100, and the angular side guide arrangement 400 is on the opposite side of the expandable interbody device 100 is configured to angle rearwardly toward the rear end of the expandable interbody device 100. The drive block or core 110 includes a guide flange 500 on each side of the drive block or core 110, which guide flange is configured to slide within the angular side guide arrangement 400 on each of the top and bottom endplates 120, 130 as the top and bottom endplates 120, 130 move between the fully closed and fully expanded positions, or vice versa. The guide flange 500 on each side of the drive block or core 110 is configured to remain at least partially in the angular side guide arrangement 400 on each of the top and bottom endplates 120, 130 as the top and bottom endplates 120, 130 move between the fully closed and fully expanded positions, or vice versa. As illustrated in FIG. 20, the first left side slide 220, a second left side slide 230 almost disengage (e.g., 0.001-5% of the front face of the first left side slide 220, a second left side slide 230 engage the top and bottom endplates 120, 130 and all values and ranges therebetween) or completely disengage from the top and bottom endplates 120, 130 when the top and bottom endplates 120, 130 move to the fully expanded position. As illustrated in FIG. 21, only the top front edge and the bottom front edge of the first left side slide 220, a second left side slide 230 engage the top and bottom endplates 120, 130 when the top and bottom endplates 120, 130 move to the fully expanded position.

A number of implementations have been described. Nevertheless, it will be understood that various modifications may be made without departing from the spirit and scope of the claims. Accordingly, other implementations are within the scope of the following claims.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

To aid the Patent Office and any readers of this application and any resulting patent in interpreting the claims appended hereto, Applicant does not intend any of the appended claims or claim elements to invoke 35 U.S.C. 112 (f) unless the words "means for" or "step for" are explicitly used in the particular claim.

What is claimed:

1. An expandable interbody device; said expandable interbody device comprises a drive block, a top endplate, a bottom endplate, a first drive arrangement, and a second drive arrangement; said first drive arrangement includes a first drive screw, a first left side slide, a first upper left side linkage, and a first lower left side linkage; said first upper left side linkage is rotatably or pivotally connected to said first left side slide; said first upper left side linkage engages said top endplate; said first lower left side linkage is rotatably or pivotally connected to said first left side slide; said first lower left side linkage engages said bottom endplate; said second drive arrangement includes a second drive screw, a first right side slide, a first upper right side linkage, and a first lower right side linkage; said first upper right side linkage is rotatably or pivotally connected to said first right side slide; said first upper right side linkage engages said top endplate;

said first lower right side linkage is rotatably or pivotally connected to said first right side slide;

said first lower right side linkage engages said bottom endplate; said first left side slide is positioned on a left side portion of said expandable interbody device; said first right side slide is positioned on a right side portion of said expandable interbody device; said first drive screw and said second drive screw are independently rotatably from one another; said drive block includes left and right-side slide guides to facilitate in causing a longitudinal position of said drive block to move relative to said top and bottom endplates as said top and bottom endplates move between a fully closed and a fully expanded position.

2. The expandable interbody device as defined in claim 1, wherein said first drive arrangement further includes a second left side slide, a second upper left side linkage, and a second lower left side linkage; said second upper left side linkage is rotatably or pivotally connected to said second left side slide; said second upper left side linkage engages said top endplate; said second lower left side linkage is rotatably or pivotally connected to said second left side slide; said second lower left side linkage engages said bottom endplate; said second drive arrangement further includes a second right side slide, a second upper right side linkage, and a second lower right side linkage; said second upper right side linkage is rotatably or pivotally connected to said second right side slide; said second upper right side linkage engages said top endplate; said second lower right side linkage is rotatably or pivotally connected to said second right side slide; said second lower right side linkage engages said bottom endplate; said second left side slide is positioned on a left side portion of said expandable interbody device; said second right side slide is positioned on a right side portion of said expandable interbody device.

3. The expandable interbody device as defined in claim 2, wherein said first and second left side slides are configured to move in opposite directions when said first drive screw is rotated; said first and second right side slides are configured to move in opposite directions when said second drive screw is rotated.

4. The expandable interbody device as defined in claim 2, wherein rotation of said first drive screw causes simultaneous movement of said first and second left side slides; and wherein rotation of said second drive screw causes simultaneous movement of said first and second right side slides.

5. The expandable interbody device as defined in claim 2, wherein said first and second left side slides include an opening wherein a portion of said first drive screw is threadedly inserted therein; and said first and second right side slide include an opening wherein a portion of said second drive screw is threadedly inserted therein.

6. The expandable interbody device as defined in claim 1, wherein said drive block includes first and second screw cavities that extend along 50-100% of a longitudinal length of said drive block; at least 50% of a longitudinal length of said first and second screw cavities are spaced apart from one another; said first screw cavity is configured to receive said first drive screw; said second screw cavity is configured to receive said second drive screw.

7. The expandable interbody device as defined in claim 6, wherein said first and second screw cavities are positioned generally parallel to one another.

8. The expandable interbody device as defined in claim 1, wherein said first left side slide includes an opening wherein a portion of said first drive screw is threadedly inserted therein; and said first right side slide includes an opening wherein a portion of said second drive screw is threadedly inserted therein.

9. The expandable interbody device as defined in claim 1, wherein said first drive screw includes a non-slide region that inhibits or prevents longitudinal movement of said first drive screw along a longitudinal axis of said drive block when said first drive screw is rotated; and wherein said second drive screw includes a non-slide region that inhibits or prevents longitudinal movement of said second drive screw along said longitudinal axis of said drive block when said second drive screw is rotated.

10. The expandable interbody device as defined in claim 1, wherein a top surface of said top and/or bottom endplates incudes a textured surface.

11. The expandable interbody device as defined in claim 1, wherein a front and/or rear region of said top endplate includes a downwardly sloping surface; and wherein a front and/or rear region of said bottom endplate includes an upwardly sloping surface.

12. The expandable interbody device as defined in claim 1, wherein a top surface of said top and/or bottom endplate includes a graft window.

13. The expandable interbody device as defined in claim 1, wherein said top endplate includes left and right side flanges; and wherein said left side flange is configured to move along and adjacent to said left-side guide of said drive block when said top endplate moves between said fully closed and said fully expanded position; and wherein said right side flange is configured to move along and adjacent to said right-side guide of said drive block when said top endplate moves between said fully closed and said fully expanded position.

14. The expandable interbody device as defined in claim 1, wherein said bottom endplate includes left and right side flanges; and wherein said left side flange is configured to move along and adjacent to said left-side guide of said drive block when said bottom endplate moves between said fully closed and said fully expanded position; and wherein said right side flange is configured to move along and adjacent to said right-side guide of said drive block when said bottom endplate moves between said fully closed and said fully expanded position.

15. The expandable interbody device as defined in claim 1, wherein at least a portion of said expandable interbody device includes one or more metals selected from the group consisting of titanium, chromium, molybdenum, rhenium, niobium, tantalum, and zirconium.

16. The expandable interbody device as defined in claim 1, wherein at least a portion of said expandable interbody device is formed of a refractory metal alloy or a metal alloy that includes at least 15 atw. % rhenium.

17. The expandable interbody device as defined in claim 1, wherein at least a portion of said expandable interbody device includes one or more metal alloys selected from the group consisting of a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or 1) metal alloy that includes at least 5 awt. % rhenium.

18. The expandable interbody device as defined in claim 1, wherein one or more of said first endplate and said second endplate includes a micro-textured surface, and/or one or more teeth.

19. The expandable interbody device as defined in claim 1, wherein one or more portions of said expandable interbody device includes an enhancement layer; said enhancement layer includes one or more of chromium nitride (CrN), diamond-like carbon (DLC), titanium nitride (TiN), titanium oxynitride or titanium nitride oxide ($TiNO_x$), zirconium nitride (ZrN), zirconium oxide ($ZrO_2$), zirconium oxynitride ($ZrN_xO_y$), oxyzirconium-nitrogen-carbon (ZrNC), and/or zirconium OxyCarbide (ZrOC).

20. The expandable interbody device as defined in claim 19, wherein at least a portion of said expandable interbody device is formed of a refractory metal alloy or a metal alloy that includes at least 15 atw. % rhenium.

21. The expandable interbody device as defined in claim 19, wherein at least a portion of said expandable interbody device includes one or more metal alloys selected from the group consisting of a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or 1) metal alloy that includes at least 5 awt. % rhenium.

22. The expandable interbody device as defined in claim 19, wherein one or more portions of said expandable interbody device includes an enhancement layer; said enhancement layer includes one or more of chromium nitride (CrN), diamond-like carbon (DLC), titanium nitride (TiN), titanium oxynitride or titanium nitride oxide ($TiNO_x$), zirconium nitride (ZrN), zirconium oxide ($ZrO_2$), zirconium oxynitride ($ZrN_xO_y$), oxyzirconium-nitrogen-carbon (ZrNC), and/or zirconium OxyCarbide (ZrOC).

23. An expandable interbody device; said expandable interbody device comprises a drive block, a top endplate, a bottom endplate, a first drive arrangement, and a second drive arrangement; said first drive arrangement includes a first drive screw, a first left side slide, a second left side slide, a first upper left side linkage, a second upper left side linkage, a first lower left side linkage and a second lower left side linkage; said first upper left side linkage is rotatably or pivotally connected to said first left side slide and said top endplate; said first lower left side linkage is rotatably or pivotally connected to said first left side slide and said bottom endplate;

said second upper left side linkage is rotatably or pivotally connected to said second left side slide and said top endplate; said second lower left side linkage is rotatably or pivotally connected to said second left side slide and said bottom endplate; said second drive arrangement includes a second drive screw, a first right side slide, a second right side slide, a first upper right side linkage, a second upper right side linkage, a first lower right side linkage and a second lower right side linkage; said first upper right side linkage is rotatably or pivotally connected to said first right side slide and said top endplate; said first lower right side linkage is rotatably or pivotally connected to said first right side slide and said bottom endplate; said second upper right side linkage is rotatably or pivotally connected to said second right side slide and said top endplate; said second lower right side linkage is rotatably or pivotally connected to said second right side slide and said bottom endplate; said first left side slide is positioned on a left side portion of said expandable interbody device; said first right side slide is positioned on a right side portion of said expandable interbody device; said first drive screw and said second drive screw are independently rotatably from one another; rotation of said first drive screw causes simultaneous movement of said first and second left side slides; and wherein rotation of said second drive screw causes simultaneous movement of said first and second right side slides; said drive block includes first and second screw cavities that extend along 50-100% of a longitudinal length of said drive block; at least 50% of a longitudinal length of said first and second screw cavities are spaced apart from one another; said first screw cavity is configured to receive said first drive screw; said second screw cavity is configured to receive said second drive screw; said first and second screw cavities are positioned generally parallel to one another; rotation of said first drive screw causes movement of said first and second left side slides in opposite directions along the longitudinal axis of said drive block; and wherein rotation of said second drive screw causes movement of said first and second right side slides in opposite directions along the longitudinal axis of said drive block; said first and second left side slides each include an opening wherein a portion of said first drive screw is threadedly inserted therein; and said first and second right side slides each include an opening wherein a portion of said second drive screw is threadedly inserted therein; said first drive screw includes a non-slide region that inhibits or prevents longitudinal movement of said first drive screw in said drive block when said first drive screw is rotated; and wherein said second drive screw includes a non-slide region that inhibits or prevents longitudinal movement of said second drive screw in said drive block when said second drive screw is rotated; said drive block includes left and right side slide guides to facilitate in maintaining a longitudinal position of said top and bottom endplates relative to said drive block as said top and bottom endplates move between a fully closed and a fully expanded position; said top endplate includes left and right side flanges; and wherein said left side flange is configured to move along and adjacent to said left-side slide guide of said drive block when said top endplate moves between said fully closed and said fully expanded position; and wherein said right side flange is configured to move along and adjacent to said right-side slide guide of said drive block when said top endplate moves between said fully closed and said fully expanded position; said bottom endplate includes left and right side flanges; and wherein said left side flange is configured to move along and adjacent to said left-side slide guide of said drive block when said bottom endplate moves between said fully closed and said fully expanded position; and wherein said right side flange is configured to move along and adjacent to said right-side slide guide of said drive block when said bottom endplate moves between said fully closed and said fully expanded position.

24. The expandable interbody device as defined in claim 23, wherein a top surface of said top and/or bottom endplates incudes a textured surface.

25. The expandable interbody device as defined in claim 23, wherein a front and/or rear region of said top endplate includes a downwardly sloping surface; and wherein a front and/or rear region of said bottom endplate includes an upwardly sloping surface.

26. The expandable interbody device as defined in claim 23, wherein a top surface of said top and bottom endplate includes a graft window.

27. A method for using an expandable interbody device comprising:

providing said expandable interbody device; said expandable interbody device comprises a drive block, a top endplate, a bottom endplate, a first drive arrangement, and a second drive arrangement; said first drive arrangement includes a first drive screw, a first left side slide, a first upper left side linkage, and a first lower left side linkage; said first upper left side linkage is rotatably or pivotally connected to said first left side slide; said first upper left side linkage engages said top endplate; said first lower left side linkage is rotatably or pivotally connected to said first left side slide; said first lower left side linkage engages said bottom endplate; said second drive arrangement includes a second drive screw, a first right side slide, a first upper right side linkage, and a first lower right side linkage; said first upper right side linkage is rotatably or pivotally connected to said first right side slide; said first upper right side linkage engages said top endplate;

said first lower right side linkage is rotatably or pivotally connected to said first right side slide;

said first lower right side linkage engages said bottom endplate; said first left side slide is positioned on a left side portion of said expandable interbody device; said first right side slide is positioned on a right side portion of said expandable interbody device; said first drive screw and said second drive screw are independently rotatably from one another; said drive block includes left and right-side slide guides;

inserting said expandable interbody device into a patient; and rotating one or both of said first and second drive screws to cause movement of at least a portion of said top endplate relative to at least a portion of said bottom endplate; said left and right-side slide guides to facilitate in causing a longitudinal position of said drive block to move relative to said top and bottom endplates as said top and bottom endplates move between a fully closed and a fully expanded position.

* * * * *